(12) United States Patent
Napier

(10) Patent No.: US 6,897,050 B1
(45) Date of Patent: May 24, 2005

(54) DESATURASE GENES AND THEIR USE

(75) Inventor: Johnathan A. Napier, Long Ashton (GB)

(73) Assignee: University of Bristol, Bristol (GB)

( * ) Notice: Subject to any disclaimer, the term of this patent is extended or adjusted under 35 U.S.C. 154(b) by 0 days.

(21) Appl. No.: 09/555,093

(22) PCT Filed: Nov. 24, 1998

(86) PCT No.: PCT/GB98/03507

§ 371 (c)(1),
(2), (4) Date: Aug. 22, 2000

(87) PCT Pub. No.: WO99/27111

PCT Pub. Date: Jun. 3, 1999

(30) Foreign Application Priority Data

Nov. 24, 1997 (GB) .............................................. 9724783

(51) Int. Cl.[7] ............................. C12N 9/02; C12N 9/64; C12N 5/06
(52) U.S. Cl. ........................ 435/189; 435/226; 530/350
(58) Field of Search ................................ 435/189, 226; 530/350

(56) References Cited

U.S. PATENT DOCUMENTS 5,614,393 A * 3/1997 Thomas et al. ............. 435/134
5,968,809 A * 10/1999 Knutzon et al. ......... 435/254.2

FOREIGN PATENT DOCUMENTS

| EP | 0400547 | 12/1990 |
|---|---|---|
| EP | 0410637 | 1/1991 |
| EP | 0454102 | 10/1991 |
| WO | 96/21022 | 7/1996 |
| WO | 98/46763 | 10/1998 |
| WO | 98/46764 | 10/1998 |

OTHER PUBLICATIONS

Tanaka, T. et al. LIPIDS vol. 31, No. 11, 1996 pp. 1173–1178.
Spychalla, J.P., et al.: Proceedings of the National Academy of Sciences of USA, vol. 94, Feb. 1997, pp. 1142–1147.
Kodama H. et al.: Plant Physiology, vol. 105 Jan. 1, 1994, pp. 601–605.
Hillier, L. et al. "Pk42c09.r1 Caenorhabditis briggsae cDNA similar to SP:S35157 S35517 delta(6)–Desaturase–Synechocystis" Apr. 18, 1995.
Swinbourne, J. et al.: "caenorhabditis elegans cosmid WO8D2" Mar. 23, 1996.
Swinbourne, J. et al.: "T13F2.1" Feb. 1, 1997.
Kohara, Y.: "C. Elegans cDNA clone yk436b12 : 5' end, single read" Sep. 9, 1997.
Kohara, Y.: "C elegans cDNA clone yk43b12 : 3' end single read" Sep. 6, 1997.
Sayanova, O. et al.: Caenorhabditis elegans delta6–fatty–acid–desaturase mRNA, complete CDs Apr. 27, 1998.
Sayanova, O. et al.: Proceedings of the National Academy of Sciences of USA, vol. 94, Apr. 1997, pp. 4211–4216.

* cited by examiner

*Primary Examiner*—Rebecca E. Prouty
*Assistant Examiner*—Malgorzata A. Walicka
(74) *Attorney, Agent, or Firm*—Banner & Witcoff, Ltd.

(57) ABSTRACT cDNA encoding *C. elegans* $\Delta^6$ desaturase has been cloned and sequenced, and the $\Delta^6$ desaturase amino acid sequence has been determined: The *C. elegans* $\Delta^6$ desaturase has a surprisingly low level of sequence identity with the known borage $\Delta^6$ desaturase. The *C. elegans* $\Delta^6$ desaturase has been expressed in yeast. It and other desaturases can be cloned in host organisms (e.g. plants) and can be used to provide useful metabolites.

12 Claims, 9 Drawing Sheets

```
          10                    30                    50
           .                     .                     .
GCTCACCAAAATGGTCGTCGACAAGAATGCCTCCGGGCTTCGAATGAAGGTCGATGGCAA
            M  V  V  D  K  N  A  S  G  L  R  M  K  V  D  G  K 70                    90                   110
           .                     .                     .
ATGGCTCTACCTTAGCGAGGAATTGGTGAAGAAACATCCAGGAGGAGCTGTTATTGAACA
 W  L  Y  L  S  E  E  L  V  K  K  H  P  G  G  A  V  I  E  Q
                                  ‾‾‾‾‾‾‾‾‾‾‾‾
         130                   150                   170
           .                     .                     .
ATATAGAAATTCGGATGCTACTCATATTTTCCACGCTTTCCACGAAGGATCTTCTCAGGC
 Y  R  N  S  D  A  T  H  I  F  H  A  F  H  E  G  S  S  Q  A 190                   210                   230
           .                     .                     .
TTATAAGCAACTTGACCTTCTGAAAAAGCACGGAGAGCACGATGAATTCCTTGAGAAACA
 Y  K  Q  L  D  L  L  K  K  E  G  E  H  D  E  F  L  E  K  Q 250                   270                   290
           .                     .                     .
ATTGGAAAAGAGACTTGACAAAGTTGATATCAATGTATCAGCATATGATGTCAGTGTTGC
 L  E  K  R  L  D  K  V  D  I  N  V  S  A  Y  D  V  S  V  A 310                   330                   350
           .                     .                     .
ACAAGAAAAGAAAATGGTTGAATCATTCGAAAAACTACGACAGAAGCTTCATGATGATGG
 Q  E  K  K  M  V  E  S  F  E  K  L  R  Q  K  L  H  D  D  G 370                   390                   410
           .                     .                     .
ATTAATGAAAGCAAATGAAACATATTTCCTGTTTAAAGCGATTTCAACACTTTCAATTAT
 L  M  K  A  N  E  T  Y  F  L  F  K  A  I  S  T  L  S  I  M 430                   450                   470
           .                     .                     .
GGCATTTGCATTTTATCTTCAGTATCTTGGATGGTATATTACTTCTGCATGTTTATTAGC
 A  F  A  F  Y  L  Q  Y  L  G  W  Y  I  T  S  A  C  L  L  A 490                   510                   530
           .                     .                     .
ACTTGCATGGCAACAATTCGGATGGTTAACACATGAGTTCTGCCATCAACAGCCAACAAA
 L  A  W  Q  Q  F  G  W  L  T  H  E  F  C  H  Q  Q  P  T  K
```

FIG. 1A

```
         550                  570                 590
          .                    .                   .
GAACAGACCTTTGAATGATACTATTTCTTTGTTCTTTGGTAATTTCTTACAAGGATTTTC
 N  R  P  L  N  D  T  I  S  L  F  F  G  N  F  L  Q  G  F  S 610                  630                 650
          .                    .                   .
AAGAGATTGGTGGAAGGACAAGCATAACACTCATCACGCTGCCACAAATGTAATTGATCA
 R  D  W  W  K  D  K  H  N  T  H  H  A  A  T  N  V  I  D  H 670                  690                 710
          .                    .                   .
TGACGGTGATATCGACTTGGCACCACTTTTCGCATTTATTCCAGGAGATTTGTGCAAGTA
 D  G  D  I  D  L  A  P  L  F  A  F  I  P  G  D  L  C  K  Y 730                  750                 770
          .                    .                   .
TAAGGCCAGCTTTGAAAAAGCAATTCTCAAGATTGTACCATATCAACATCTCTATTTCAC
 K  A  S  F  E  K  A  I  L  K  I  V  P  Y  Q  H  L  Y  F  T 790                  810                 830
          .                    .                   .
CGCAATGCTTCCAATGCTCCGTTTCTCATGGACTGGTCAGTCAGTTCAATGGGTATTCAA
 A  M  L  P  M  L  R  F  S  W  T  G  Q  S  V  Q  W  V  F  K 850                  870                 890
          .                    .                   .
AGaGAATCAAATGGAGTACAAGGTCTATCAAAGAAATGCATTCTGGGAGCAAGCAACAAT
 E  N  Q  M  E  Y  K  V  Y  Q  R  N  A  F  W  E  Q  A  T  I 910                  930                 950
          .                    .                   .
TGTTGGACATTGGGCTTGGGTATTCTATCAATTGTTCTTATTACCAACATGGCCACTTCG
 V  G  H  W  A  W  V  F  Y  Q  L  F  L  L  P  T  W  P  L  R 970                  990                1010
          .                    .                   .
GGTTGCTTATTTCATTATTTCACAAATGGGAGGAGGCCTTTTGATTGCTCACGTAGTCAC
 V  A  Y  F  I  I  S  Q  M  G  G  G  L  L  I  A  H  V  V  T
```

FIG. 1B

```
         1030                  1050                  1070
           .                     .                     .
TTTCAACCATAACTCTGTTGATAAGTATCCAGCCAATTCTCGAATTTTAAACAACTTCGC
 F  N  H  N  S  V  D  K  Y  P  A  N  S  R  I  L  N  N  F  A 1090                  1110                  1130
           .                     .                     .
CGCTCTTCAAATTTTGACCACACGCAACATGACTCCATCTCCATTCATTGATTGGCTTTG
 A  L  Q  I  L  T  T  R  N  M  T  P  S  P  F  I  D  W  L  W 1150                  1170                  1190
           .                     .                     .
GGGTGGACTCAATTATCAGATCGAGCACCACTTGTTCCCAACAATGCCACGTTGCAATCT
 G  G  L  N  Y  Q  I  E  H  H  L  P  P  T  M  P  R  C  N  L
              ─────────────────────

1210                  1230                  1250
           .                     .                     .
GAATGCTTGCGTGAAATATGTGAAAGAATGGTGCAAAGAGAATAATCTTCCTTACCTCGT
 N  A  C  V  K  Y  V  K  E  W  C  K  E  N  N  L  P  Y  L  V 1270                  1290                  1310
           .                     .                     .
CGATGACTACTTTGACGGATATGCAATGAATTTGCAACAATTGAAAAATATGGCTGAGCA
 D  D  Y  F  D  G  Y  A  M  N  L  Q  Q  L  K  N  M  A  E  H 1330                  1350                  1370
           .                     .                     .
CATTCAAGCTAAAGCTGCCTAAACAATCTGGGTGTTCAAAAAGTTTTTTCTTGTTTTTT
 I  Q  A  K  A  A  *

1390                  1410                  1430
           .                     .                     .
AAATTTAATTCTTTGAAATTATTTGTTTTCCGTCATTCTTCCTCCATTCCCTTTTCTGGT

1450
           .
AGAAATAAAACCTTGTTTTTCAA
```

RESULTS OF PBM SEARCH USING THE wileynbs LIBRARY

Run =DOM10004 Scan=738 (Sub) 100%=413600 ADC Mass Range=40-456
23 Sep 97 3:50 Compacted SLRP +EI 1UL C.E O/N INDUCTION + LA

| Serial | Rel. (Sim) | Rel. (Same) | Mol. Wt. | Formula & Name |
|---|---|---|---|---|
| 77275 | 99 | 81 | 292 | C19 H32 O2 6, 9, 12-Octadecatrienoic acid, methyl ester |
| 81040 | 95 | 74 | 122 | C9 H14 1, 4-Cyclononadiene |
| 43157 | 95 | 74 | 292 | C19 H32 O2 6, 9, 12-Octadecatrienoic acid, methyl ester |
| 77274 | 93 | 68 | 292 | C19 H32 O2 6, 9, 12-Octadecatrienoic acid, methyl ester |
| 6892 | 60 | 35 | 136 | C10 H16 .BETA.-FENCHENE |
| 4278 | 59 | 33 | 122 | C9 H14 3-Nonen-1-yne, (z)- |
| 25116 | 55 | 29 | 206 | C15 H26 5-Pentadecen-7-yne, (z)- |
| 17742 | 55 | 29 | 178 | C13 H22 3-Tridecen-1-yne, (z)- |
| 13423 | 55 | 29 | 162 | C12 H18 1, 4, 8-Dodecatriene, (E, E, E)- |
| 10169 | 34 | 11 | 150 | C11 H18 Cyclopropane, 1-etheny-2-hexenyl-, 1.alpha., 2.beta. (E) |
| 2366 | 33 | 10 | 108 | C8 H12 1, 4-Cyclooctadiene, (z, z)- |
| 2372 | 32 | 9 | 108 | C8 H12 Bicyclo 5.1.0. oct-3-ene |
| 6909 | 24 | 6 | 136 | C10 H16 Cyclooctene, 3-ethenyl- |
| 10171 | 23 | 6 | 150 | C11 H18 Cyclohexene, 3-(3-methyl-1-butenyl)-, (E)- |
| 29046 | 23 | 6 | 222 | C15 H26 O 5, 10-Pentadecadienal, (z, z)- |
| 17743 | 21 | 5 | 178 | C13 H22 3-Tridecen-1-yne, (E)- |
| 10173 | 20 | 4 | 150 | C11 H18 Spiro 5.5.undec-1-ene |
| 4281 | 20 | 4 | 122 | C9 H14 Bicyclo 5.1.0. octane, 8-methylene- |
| 10192 | 18 | 3 | 150 | C11 H18 (-)-2-METHYL-2-BORNENE |
| 4291 | 18 | 3 | 122 | C9 H14 1, 2-CYCLONONADIENE |
| 2597 | 18 | 3 | 110 | C8 H14 Cyclopentane, (1-methylethylidene)- |
| 7335 | 12 | 2 | 138 | C10 H18 4-Decyne |
| 67891 | 11 | 2 | 82 | C6 H10 Cyclopropane, 1, 2-dimethyl-3-methylene-, cis- |
| 618 | 11 | 2 | 82 | C6 H10 Cyclopropane, 1, 2-dimethyl-3-methylene-, trans- |
| 71289 | 4 | 1 | 136 | C10 H16 2-.BETA.-PINENE |

Run =DOM10004 Scan=738 (Sub) 100%=413600 ADC Mass Range=40-456
23 Sep 97 3:50 Compacted SLRP +EI 1UL C.E O/N INDUCTION + LA

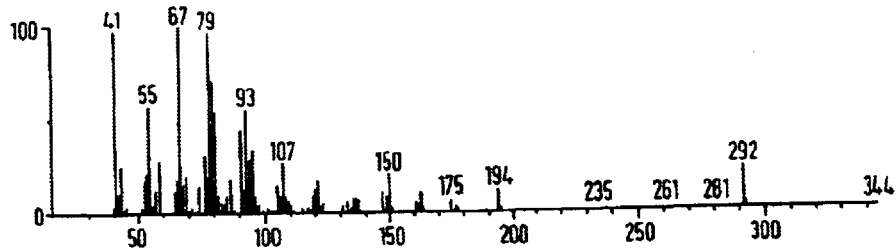

wileynbs: 77275 Rel(sim):99 Rel(same):81
6,9,12-Octadecatrienoic acid, methyl ester
C19 H32 O2 MW=292.240230 CAS=2676417

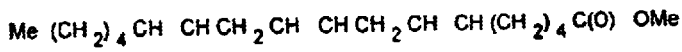

FIG. 4

SEQUENCE LISTING

<160> NUMBER OF SEQ ID NOS: 8

<210> SEQ ID NO 1
<211> LENGTH: 1462
<212> TYPE: DNA
<213> ORGANISM: C. elegans
<220> FEATURE:
<221> NAME/KEY: CDS
<222> LOCATION: (11)...(1340)

<400> SEQUENCE: 1

```
gctcaccaaa atg gtc gtc gac aag aat gcc tcc ggg ctt cga atg aag           49
           Met Val Val Asp Lys Asn Ala Ser Gly Leu Arg Met Lys
             1               5                  10 gtc gat ggc aaa tgg ctc tac ctt agc gag gaa ttg gtg aag aaa cat          97
Val Asp Gly Lys Trp Leu Tyr Leu Ser Glu Glu Leu Val Lys Lys His
         15                  20                  25 cca gga gga gct gtt att gaa caa tat aga aat tcg gat gct act cat         145
Pro Gly Gly Ala Val Ile Glu Gln Tyr Arg Asn Ser Asp Ala Thr His
 30                  35                  40                  45 att ttc cac gct ttc cac gaa gga tct tct cag gct tat aag caa ctt         193
Ile Phe His Ala Phe His Glu Gly Ser Ser Gln Ala Tyr Lys Gln Leu
                 50                  55                  60 gac ctt ctg aaa aag cac gga gag cac gat gaa ttc ctt gag aaa caa         241
Asp Leu Leu Lys Lys His Gly Glu His Asp Glu Phe Leu Glu Lys Gln
             65                  70                  75 ttg gaa aag aga ctt gac aaa gtt gat atc aat gta tca gca tat gat         289
Leu Glu Lys Arg Leu Asp Lys Val Asp Ile Asn Val Ser Ala Tyr Asp
         80                  85                  90 gtc agt gtt gca caa gaa aag aaa atg gtt gaa tca ttc gaa aaa cta         337
Val Ser Val Ala Gln Glu Lys Lys Met Val Glu Ser Phe Glu Lys Leu
     95                 100                 105 cga cag aag ctt cat gat gat gga tta atg aaa gca aat gaa aca tat         385
Arg Gln Lys Leu His Asp Asp Gly Leu Met Lys Ala Asn Glu Thr Tyr
110                 115                 120                 125 ttc ctg ttt aaa gcg att tca aca ctt tca att atg gca ttt gca ttt         433
Phe Leu Phe Lys Ala Ile Ser Thr Leu Ser Ile Met Ala Phe Ala Phe
                130                 135                 140 tat ctt cag tat ctt gga tgg tat att act tct gca tgt tta tta gca         481
Tyr Leu Gln Tyr Leu Gly Trp Tyr Ile Thr Ser Ala Cys Leu Leu Ala
            145                 150                 155 ctt gca tgg caa caa ttc gga tgg tta aca cat gag ttc tgc cat caa         529
Leu Ala Trp Gln Gln Phe Gly Trp Leu Thr His Glu Phe Cys His Gln
        160                 165                 170 cag cca aca aag aac aga cct ttg aat gat act att tct ttg ttc ttt         577
Gln Pro Thr Lys Asn Arg Pro Leu Asn Asp Thr Ile Ser Leu Phe Phe
    175                 180                 185 ggt aat ttc tta caa gga ttt tca aga gat tgg tgg aag gac aag cat         625
Gly Asn Phe Leu Gln Gly Phe Ser Arg Asp Trp Trp Lys Asp Lys His
190                 195                 200                 205 aac act cat cac gct gcc aca aat gta att gat cat gac ggt gat atc         673
Asn Thr His His Ala Ala Thr Asn Val Ile Asp His Asp Gly Asp Ile
                210                 215                 220 gac ttg gca cca ctt ttc gca ttt att cca gga gat ttg tgc aag tat         721
Asp Leu Ala Pro Leu Phe Ala Phe Ile Pro Gly Asp Leu Cys Lys Tyr
            225                 230                 235 aag gcc agc ttt gaa aaa gca att ctc aag att gta cca tat caa cat         769
Lys Ala Ser Phe Glu Lys Ala Ile Leu Lys Ile Val Pro Tyr Gln His
        240                 245                 250
```

```
ctc tat ttc acc gca atg ctt cca atg ctc cgt ttc tca tgg act ggt        817
Leu Tyr Phe Thr Ala Met Leu Pro Met Leu Arg Phe Ser Trp Thr Gly
    255                 260                 265 cag tca gtt caa tgg gta ttc aaa gag aat caa atg gag tac aag gtc        865
Gln Ser Val Gln Trp Val Phe Lys Glu Asn Gln Met Glu Tyr Lys Val
270                 275                 280                 285 tat caa aga aat gca ttc tgg gag caa gca aca att gtt gga cat tgg        913
Tyr Gln Arg Asn Ala Phe Trp Glu Gln Ala Thr Ile Val Gly His Trp
                290                 295                 300 gct tgg gta ttc tat caa ttg ttc tta tta cca aca tgg cca ctt cgg        961
Ala Trp Val Phe Tyr Gln Leu Phe Leu Leu Pro Thr Trp Pro Leu Arg
                305                 310                 315 gtt gct tat ttc att att tca caa atg gga gga ggc ctt ttg att gct       1009
Val Ala Tyr Phe Ile Ile Ser Gln Met Gly Gly Gly Leu Leu Ile Ala
                320                 325                 330 cac gta gtc act ttc aac cat aac tct gtt gat aag tat cca gcc aat       1057
His Val Val Thr Phe Asn His Asn Ser Val Asp Lys Tyr Pro Ala Asn
                335                 340                 345 tct cga att tta aac aac ttc gcc gct ctt caa att ttg acc aca cgc       1105
Ser Arg Ile Leu Asn Asn Phe Ala Ala Leu Gln Ile Leu Thr Thr Arg
350                 355                 360                 365 aac atg act cca tct cca ttc att gat tgg ctt tgg ggt gga ctc aat       1153
Asn Met Thr Pro Ser Pro Phe Ile Asp Trp Leu Trp Gly Gly Leu Asn
                370                 375                 380 tat cag atc gag cac cac ttg ttc cca aca atg cca cgt tgc aat ctg       1201
Tyr Gln Ile Glu His His Leu Phe Pro Thr Met Pro Arg Cys Asn Leu
                385                 390                 395 aat gct tgc gtg aaa tat gtg aaa gaa tgg tgc aaa gag aat aat ctt       1249
Asn Ala Cys Val Lys Tyr Val Lys Glu Trp Cys Lys Glu Asn Asn Leu
                400                 405                 410 cct tac ctc gtc gat gac tac ttt gac gga tat gca atg aat ttg caa       1297
Pro Tyr Leu Val Asp Asp Tyr Phe Asp Gly Tyr Ala Met Asn Leu Gln
                415                 420                 425 caa ttg aaa aat atg gct gag cac att caa gct aaa gct gcc t             1340
Gln Leu Lys Asn Met Ala Glu His Ile Gln Ala Lys Ala Ala
430                 435                 440 aaacaatctg ggtgttcaaa aagttttttc ttgtttttta aatttaattc tttgaaatta     1400
tttgttttcc gtcattcttc ctccattccc ttttctggta gaaataaaac cttgtttttc     1460
aa                                                                    1462

<210> SEQ ID NO 2
<211> LENGTH: 443
<212> TYPE: PRT
<213> ORGANISM: C. elegans

<400> SEQUENCE: 2

Met Val Val Asp Lys Asn Ala Ser Gly Leu Arg Met Lys Val Asp Gly
1               5                   10                  15

Lys Trp Leu Tyr Leu Ser Glu Glu Leu Val Lys His Pro Gly Gly
            20                  25                  30

Ala Val Ile Glu Gln Tyr Arg Asn Ser Asp Ala Thr His Ile Phe His
                35                  40                  45

Ala Phe His Glu Gly Ser Ser Gln Ala Tyr Lys Gln Leu Asp Leu Leu
        50                  55                  60

Lys Lys His Gly Glu His Asp Glu Phe Leu Glu Lys Gln Leu Glu Lys
65                  70                  75                  80

Arg Leu Asp Lys Val Asp Ile Asn Val Ser Ala Tyr Asp Val Ser Val
                85                  90                  95
```

```
Ala Gln Glu Lys Lys Met Val Glu Ser Phe Glu Lys Leu Arg Gln Lys
                100                 105                 110

Leu His Asp Asp Gly Leu Met Lys Ala Asn Glu Thr Tyr Phe Leu Phe
            115                 120                 125

Lys Ala Ile Ser Thr Leu Ser Ile Met Ala Phe Ala Phe Tyr Leu Gln
        130                 135                 140

Tyr Leu Gly Trp Tyr Ile Thr Ser Ala Cys Leu Leu Ala Leu Ala Trp
145                 150                 155                 160

Gln Gln Phe Gly Trp Leu Thr His Glu Phe Cys His Gln Gln Pro Thr
                165                 170                 175

Lys Asn Arg Pro Leu Asn Asp Thr Ile Ser Leu Phe Phe Gly Asn Phe
            180                 185                 190

Leu Gln Gly Phe Ser Arg Asp Trp Trp Lys Asp Lys His Asn Thr His
        195                 200                 205

His Ala Ala Thr Asn Val Ile Asp His Asp Gly Asp Ile Asp Leu Ala
210                 215                 220

Pro Leu Phe Ala Phe Ile Pro Gly Asp Leu Cys Lys Tyr Lys Ala Ser
225                 230                 235                 240

Phe Glu Lys Ala Ile Leu Lys Ile Val Pro Tyr Gln His Leu Tyr Phe
                245                 250                 255

Thr Ala Met Leu Pro Met Leu Arg Phe Ser Trp Thr Gly Gln Ser Val
            260                 265                 270

Gln Trp Val Phe Lys Glu Asn Gln Met Glu Tyr Lys Val Tyr Gln Arg
        275                 280                 285

Asn Ala Phe Trp Glu Gln Ala Thr Ile Val Gly His Trp Ala Trp Val
290                 295                 300

Phe Tyr Gln Leu Phe Leu Pro Thr Trp Pro Leu Arg Val Ala Tyr
305                 310                 315                 320

Phe Ile Ile Ser Gln Met Gly Gly Leu Leu Ile Ala His Val Val
                325                 330                 335

Thr Phe Asn His Asn Ser Val Asp Lys Tyr Pro Ala Asn Ser Arg Ile
            340                 345                 350

Leu Asn Asn Phe Ala Ala Leu Gln Ile Leu Thr Thr Arg Asn Met Thr
        355                 360                 365

Pro Ser Pro Phe Ile Asp Trp Leu Trp Gly Gly Leu Asn Tyr Gln Ile
370                 375                 380

Glu His His Leu Phe Pro Thr Met Pro Arg Cys Asn Leu Asn Ala Cys
385                 390                 395                 400

Val Lys Tyr Val Lys Glu Trp Cys Lys Glu Asn Asn Leu Pro Tyr Leu
                405                 410                 415

Val Asp Asp Tyr Phe Asp Gly Tyr Ala Met Asn Leu Gln Gln Leu Lys
            420                 425                 430

Asn Met Ala Glu His Ile Gln Ala Lys Ala Ala
        435                 440

<210> SEQ ID NO 3
<211> LENGTH: 27
<212> TYPE: PRT
<213> ORGANISM: Artificial Sequence
<220> FEATURE:
<223> OTHER INFORMATION: cytochrome b5 domain
<221> NAME/KEY: VARIANT
<222> LOCATION: (1)...(27)
<223> OTHER INFORMATION: Xaa = Any Amino Acid

<400> SEQUENCE: 3
```

```
His Pro Gly Gly Xaa Xaa Xaa Xaa Xaa Xaa Xaa Xaa Xaa Xaa
 1               5                  10                 15

Xaa Xaa Xaa Phe Xaa Xaa Xaa Xaa Xaa His
            20              25
```

<210> SEQ ID NO 4
<211> LENGTH: 443
<212> TYPE: PRT
<213> ORGANISM: C. elegans

<400> SEQUENCE: 4

```
Met Val Val Asp Lys Asn Ala Ser Gly Leu Arg Met Lys Val Asp Gly
 1               5                  10                  15

Lys Trp Leu Tyr Leu Ser Glu Glu Leu Val Lys His Pro Gly Gly
                20                  25                  30

Ala Val Ile Glu Gln Tyr Arg Asn Ser Asp Ala Thr His Ile Phe His
                35                  40                  45

Ala Phe His Glu Gly Ser Ser Gln Ala Tyr Lys Gln Leu Asp Leu Leu
 50                  55                  60

Lys Lys His Gly Glu His Asp Glu Phe Leu Lys Gln Leu Glu Lys
 65                  70                  75                  80

Arg Leu Asp Lys Val Asp Ile Asn Val Ser Ala Tyr Asp Val Ser Val
                    85                  90                  95

Ala Gln Glu Lys Lys Met Val Glu Ser Phe Glu Lys Leu Arg Gln Lys
                100                 105                 110

Leu His Asp Asp Gly Leu Met Lys Ala Asn Glu Thr Tyr Phe Leu Phe
                115                 120                 125

Lys Ala Ile Ser Thr Leu Ser Ile Met Ala Phe Ala Phe Tyr Leu Gln
            130                 135                 140

Tyr Leu Gly Trp Tyr Ile Thr Ser Ala Cys Leu Leu Ala Leu Ala Trp
145                 150                 155                 160

Gln Gln Phe Gly Trp Leu Thr His Glu Phe Cys His Gln Gln Pro Thr
                    165                 170                 175

Lys Asn Arg Pro Leu Asn Asp Thr Ile Ser Leu Phe Phe Gly Asn Phe
                180                 185                 190

Leu Gln Gly Phe Ser Arg Asp Trp Trp Lys Asp Lys His Asn Thr His
                195                 200                 205

His Ala Ala Thr Asn Val Ile Asp His Asp Gly Asp Ile Asp Leu Ala
            210                 215                 220

Phe Leu Phe Ala Phe Ile Pro Gly Asp Leu Cys Lys Tyr Lys Ala Ser
225                 230                 235                 240

Phe Glu Lys Ala Ile Leu Lys Ile Val Pro Tyr Gln His Leu Tyr Phe
                245                 250                 255

Thr Ala Met Leu Pro Met Leu Arg Phe Ser Trp Thr Gly Gln Ser Val
                260                 265                 270

Gln Trp Val Phe Lys Glu Asn Gln Met Glu Tyr Lys Val Tyr Gln Arg
            275                 280                 285

Asn Ala Phe Trp Glu Gln Ala Thr Ile Val Gly His Trp Ala Trp Val
            290                 295                 300

Phe Tyr Gln Leu Phe Leu Pro Thr Trp Pro Leu Arg Val Ala Tyr
305                 310                 315                 320

Phe Ile Ile Ser Gln Met Gly Gly Leu Leu Ile Ala His Val Val
                    325                 330                 335

Thr Phe Asn His Asn Ser Val Asp Lys Tyr Pro Ala Asn Ser Arg Ile
```

-continued

```
                    340                 345                 350
Leu Asn Asn Phe Ala Ala Leu Gln Ile Leu Thr Thr Arg Asn Met Thr
            355                 360                 365

Pro Ser Pro Phe Ile Asp Trp Leu Trp Gly Gly Leu Asn Tyr Gln Ile
        370                 375                 380

Glu His His Leu Phe Pro Thr Met Pro Arg Cys Asn Leu Asn Ala Cys
385                 390                 395                 400

Val Lys Tyr Val Lys Glu Trp Cys Lys Glu Asn Asn Leu Pro Tyr Leu
                405                 410                 415

Val Asp Asp Tyr Phe Asp Gly Tyr Ala Met Asn Leu Gln Gln Leu Lys
            420                 425                 430

Asn Met Ala Glu His Ile Gln Ala Lys Ala Ala
        435                 440
```

<210> SEQ ID NO 5
<211> LENGTH: 471
<212> TYPE: PRT
<213> ORGANISM: C. elegans

<400> SEQUENCE: 5

```
Met Val Val Asp Lys Ala Ser Gly Leu Arg Met Lys Val Asp Gly Lys
  1               5                  10                  15

Trp Leu Tyr Leu Ser Glu Glu Leu Val Lys His Pro Gly Gly Ala
                20                  25                  30

Val Ile Glu Gln Tyr Ser Ile Pro Pro Leu Asn Lys Asn Ile Glu Thr
            35                  40                  45

Arg Gly Ile Ile Thr Thr Arg Gly Ser Ser Asn Ala Leu Asp Ile Leu
        50                  55                  60

Tyr Phe Tyr Arg Asn Ser Asp Ala Thr His Ile Phe His Ala Phe His
 65                  70                  75                  80

Glu Gly Ser Ser Gln Ala Tyr Lys Gln Leu Asp Leu Leu Lys Lys His
                 85                  90                  95

Gly Glu His Asp Glu Phe Leu Glu Lys Gln Leu Glu Lys Arg Leu Asp
            100                 105                 110

Lys Val Asp Ile Asn Val Ser Ala Tyr Asp Val Ser Val Gln Glu Lys
        115                 120                 125

Lys Met Val Glu Ser Phe Glu Lys Leu Arg Gln Lys Leu His Asp Asp
    130                 135                 140

Gly Leu Met Lys Ala Asn Glu Thr Tyr Phe Leu Phe Lys Ala Ile Ser
145                 150                 155                 160

Thr Leu Ser Ile Met Ala Phe Ala Phe Tyr Leu Gln Tyr Leu Gly Trp
                165                 170                 175

Tyr Ile Thr Ser Ala Cys Leu Leu Ala Leu Ala Trp Gln Gln Phe Gly
            180                 185                 190

Trp Leu Thr His Glu Phe Cys His Gln Gln Pro Thr Lys Asn Arg Pro
        195                 200                 205

Leu Asn Asp Thr Ile Ser Leu Phe Phe Gly Asn Phe Leu Gln Gly Phe
    210                 215                 220

Ser Arg Asp Trp Trp Lys Asp Lys His Asn Thr His His Ala Ala Thr
225                 230                 235                 240

Asn Val Ile Asp His Asp Gly Asp Ile Asp Leu Ala Phe Leu Phe Ala
                245                 250                 255

Phe Ile Pro Gly Asp Leu Cys Lys Tyr Lys Ala Ser Phe Glu Lys Ala
            260                 265                 270
```

```
Ile Leu Lys Ile Val Pro Tyr Gln His Leu Tyr Phe Thr Ala Met Leu
            275                 280                 285

Pro Met Leu Arg Phe Ser Trp Thr Gly Gln Ser Val Gln Trp Val Phe
    290                 295                 300

Lys Glu Asn Gln Met Glu Tyr Lys Val Tyr Gln Arg Asn Ala Phe Trp
305                 310                 315                 320

Glu Gln Ala Thr Ile Val Gly His Trp Ala Trp Val Phe Tyr Gln Leu
                325                 330                 335

Phe Leu Leu Pro Thr Trp Pro Leu Arg Val Ala Tyr Phe Ile Ile Ser
            340                 345                 350

Gln Met Gly Gly Gly Leu Leu Ile Ala His Val Val Thr Phe Asn His
        355                 360                 365

Asn Ser Val Asp Lys Tyr Pro Ala Asn Ser Arg Ile Leu Asn Asn Phe
370                 375                 380

Ala Ala Leu Gln Ile Leu Thr Thr Arg Asn Met Thr Pro Ser Pro Phe
385                 390                 395                 400

Ile Asp Trp Leu Trp Gly Gly Leu Asn Tyr Gln Ile Glu His His Leu
                405                 410                 415

Phe Pro Thr Met Pro Arg Cys Asn Leu Asn Ala Cys Met Lys Tyr Val
            420                 425                 430

Lys Glu Trp Cys Lys Glu Asn Asn Leu Pro Tyr Leu Val Asp Asp Tyr
        435                 440                 445

Phe Asp Gly Tyr Ala Met Asn Leu Gln Gln Leu Lys Asn Met Ala Glu
    450                 455                 460

His Ile Gln Ala Lys Ala Ala
465                 470

<210> SEQ ID NO 6
<211> LENGTH: 443
<212> TYPE: PRT
<213> ORGANISM: Borage

<400> SEQUENCE: 6

Met Val Val Asp Lys Asn Ala Ser Gly Leu Arg Met Lys Val Asp Gly
1               5                   10                  15

Lys Trp Leu Tyr Leu Ser Glu Glu Leu Val Lys Lys His Pro Gly Gly
            20                  25                  30

Ala Val Ile Glu Gln Tyr Arg Asn Ser Asp Ala Thr His Ile Phe His
        35                  40                  45

Ala Phe His Glu Gly Ser Ser Gln Ala Tyr Lys Gln Leu Asp Leu Leu
    50                  55                  60

Lys Lys His Gly Glu His Asp Glu Phe Leu Glu Lys Gln Leu Glu Lys
65                  70                  75                  80

Arg Leu Asp Lys Val Asp Ile Asn Val Ser Ala Tyr Asp Val Ser Val
                85                  90                  95

Ala Gln Glu Lys Lys Met Val Glu Ser Phe Glu Lys Leu Arg Gln Lys
            100                 105                 110

Leu His Asp Asp Gly Leu Met Lys Ala Asn Glu Thr Tyr Phe Leu Phe
        115                 120                 125

Lys Ala Ile Ser Thr Leu Ser Ile Met Ala Phe Ala Phe Tyr Leu Gln
    130                 135                 140

Tyr Leu Gly Trp Tyr Ile Thr Ser Ala Cys Leu Leu Ala Leu Ala Trp
145                 150                 155                 160

Gln Gln Phe Gly Trp Leu Thr His Glu Phe Cys His Gln Gln Pro Thr
                165                 170                 175
```

```
Lys Asn Arg Pro Leu Asn Asp Thr Ile Ser Leu Phe Phe Gly Asn Phe
            180                 185                 190

Leu Gln Gly Phe Ser Arg Asp Trp Trp Lys Asp Lys His Asn Thr His
        195                 200                 205

His Ala Ala Thr Asn Val Ile Asp His Asp Gly Asp Ile Asp Leu Ala
    210                 215                 220

Pro Leu Phe Ala Phe Ile Pro Gly Asp Leu Cys Lys Tyr Lys Ala Ser
225                 230                 235                 240

Phe Glu Lys Ala Ile Leu Lys Ile Val Pro Tyr Gln His Leu Tyr Phe
                245                 250                 255

Thr Ala Met Leu Pro Met Leu Arg Phe Ser Trp Thr Gly Gln Ser Val
            260                 265                 270

Gln Trp Val Phe Lys Glu Asn Gln Met Glu Tyr Lys Val Tyr Gln Arg
        275                 280                 285

Asn Ala Phe Trp Glu Gln Ala Thr Ile Val Gly His Trp Ala Trp Val
    290                 295                 300

Phe Tyr Gln Leu Phe Leu Leu Pro Thr Trp Pro Leu Arg Val Ala Tyr
305                 310                 315                 320

Phe Ile Ile Ser Gln Met Gly Gly Gly Leu Leu Ile Ala His Val Val
                325                 330                 335

Thr Phe Asn His Asn Ser Val Asp Lys Tyr Pro Ala Asn Ser Arg Ile
            340                 345                 350

Leu Asn Asn Phe Ala Ala Leu Gln Ile Leu Thr Thr Arg Asn Met Thr
        355                 360                 365

Pro Ser Pro Phe Ile Asp Trp Leu Trp Gly Gly Leu Asn Tyr Gln Ile
    370                 375                 380

Glu His His Leu Phe Pro Thr Met Pro Arg Cys Asn Leu Asn Ala Cys
385                 390                 395                 400

Val Lys Tyr Val Lys Glu Trp Cys Lys Glu Asn Asn Leu Pro Tyr Leu
                405                 410                 415

Val Asp Asp Tyr Phe Asp Gly Tyr Ala Met Asn Leu Gln Gln Leu Lys
            420                 425                 430

Asn Met Ala Glu His Ile Gln Ala Lys Ala Ala
        435                 440

<210> SEQ ID NO 7
<211> LENGTH: 447
<212> TYPE: PRT
<213> ORGANISM: C. elegans

<400> SEQUENCE: 7

Met Ala Ala Gln Ile Lys Lys Tyr Ile Thr Ser Asp Leu Lys Asn His
1               5                   10                  15

Asp Lys Pro Gly Asp Leu Trp Ile Ser Ile Gln Gly Lys Ala Tyr Asp
            20                  25                  30

Val Ser Asp Trp Val Lys Asp His Pro Gly Gly Ser Phe Pro Leu Lys
        35                  40                  45

Ser Leu Ala Gly Gln Glu Val Thr Asp Ala Phe Val Ala Phe His Pro
    50                  55                  60

Ala Ser Thr Trp Lys Asn Leu Asp Lys Phe Phe Thr Gly Tyr Tyr Leu
65                  70                  75                  80

Lys Asp Tyr Ser Val Ser Glu Val Ser Lys Asp Tyr Arg Lys Leu Val
                85                  90                  95

Phe Glu Phe Ser Lys Met Gly Leu Tyr Asp Lys Lys Gly His Ile Met
```

```
                100             105             110
Phe Ala Thr Leu Cys Phe Ile Ala Met Leu Phe Ala Met Ser Val Tyr
            115             120             125

Gly Val Leu Phe Cys Glu Gly Val Leu Val His Leu Phe Ser Gly Cys
        130             135             140

Leu Met Gly Phe Leu Trp Ile Gln Ser Gly Trp Ile Gly His Asp Ala
145             150             155             160

Gly His Tyr Met Val Val Ser Asp Ser Arg Leu Asn Lys Phe Met Gly
                165             170             175

Ile Phe Ala Ala Asn Cys Leu Ser Gly Ile Ser Ile Gly Trp Trp Lys
            180             185             190

Trp Asn His Asn Ala His His Ile Ala Cys Asn Ser Leu Glu Tyr Asp
            195             200             205

Pro Asp Leu Gln Tyr Ile Pro Phe Leu Val Val Ser Ser Lys Phe Phe
            210             215             220

Gly Ser Leu Thr Ser His Phe Tyr Glu Lys Arg Leu Thr Phe Asp Ser
225             230             235             240

Leu Ser Arg Phe Phe Val Ser Tyr Gln His Trp Thr Phe Tyr Pro Ile
            245             250             255

Met Cys Ala Ala Arg Leu Asn Met Tyr Val Gln Ser Leu Ile Met Leu
            260             265             270

Leu Thr Lys Arg Asn Val Ser Tyr Arg Ala His Glu Leu Leu Gly Cys
            275             280             285

Leu Val Phe Ser Ile Trp Tyr Pro Leu Leu Val Ser Cys Leu Pro Asn
            290             295             300

Trp Gly Glu Arg Ile Met Phe Val Ile Ala Ser Leu Ser Val Thr Gly
305             310             315             320

Met Gln Gln Val Gln Phe Ser Leu Asn His Phe Ser Ser Val Tyr
                325             330             335

Val Gly Lys Pro Lys Gly Asn Asn Trp Phe Glu Lys Gln Thr Asp Gly
            340             345             350

Thr Leu Asp Ile Ser Cys Pro Pro Trp Met Asp Trp Phe His Gly Gly
            355             360             365

Leu Gln Phe Gln Ile Glu His His Leu Phe Pro Lys Met Pro Arg Cys
        370             375             380

Asn Leu Arg Lys Ile Ser Pro Tyr Val Ile Glu Leu Cys Lys Lys His
385             390             395             400

Asn Leu Pro Tyr Asn Tyr Ala Ser Phe Ser Lys Ala Asn Glu Met Thr
                405             410             415

Leu Arg Thr Leu Arg Asn Thr Ala Leu Gln Ala Arg Asp Ile Thr Lys
            420             425             430

Pro Leu Pro Lys Asn Leu Val Trp Glu Ala Leu His Thr His Gly
        435             440             445

<210> SEQ ID NO 8
<211> LENGTH: 4
<212> TYPE: PRT
<213> ORGANISM: Artificial Sequence
<220> FEATURE:
<223> OTHER INFORMATION: cytochrome b5 motif

<400> SEQUENCE: 8

His Pro Gly Gly
 1
```

DESATURASE GENES AND THEIR USE

This application is a 371 of PCT/GB98/03507 filed Nov. 24, 1998.

The present invention relates, inter alia, to novel desaturases and to uses thereof.

Over the last few years a number of microsomal and soluble fatty acid desaturases have been isolated from higher plants, most notably from *Arabidopsis thaliana*. This has resulted from a combined genetic and biochemical approach to the generation and complementation of mutant *Arabidopsis* lines defective in fatty acid desaturation or elongation (Somerville C, Browse J (1996) *Trends Cell Biol.* 6, 148–1153). The importance of this approach has been validated by the isolation and characterisation of genes encoding microsomal desaturases such as the $\Delta^{12}$ (Okuley J. et al, (1994), *Plant Cell* 6. 147–158) and $\Delta^{15}$ (Arondel V, et al, (1992) *Science* 258, 1353–1355) desaturases (encoded by the FAD2 and FAD3 genes respectively), enzymes which had previously proved intractable to classical purification techniques on account of their hydrophobicity. The isolation of these and related enzymes, such as the $\Delta^{12}$ hydroxylase from *Ricinus communis* (van de Loo FN et al (1995) *Proc. Natl. Acad. Sci* USA 92, 6743–6747). has allowed the identification of a number of conserved motifs in plant microsomal desaturases, most notably the so-called "histidine boxes" (Shanklin, J et al (1997) *Proc Natl. Acad. Sci* USA. 92, 6743–6747). Proteins containing these motifs can be classified as di-iron centre-containing enzymes (Shanklin, J et al (1997) *Proc. Natl. Acad Sci.* USA 94, 2981–1986).

WO93/11245 (Du Pont) discloses various nucleic acid fragments encoding desaturases, particularly $\Delta^{12}$ and $\Delta^{15}$ desatursase, which have been isolated from various plants. Recently a cDNA clone was isolated from the plant borage, (*Borago officinalis*) which accumulates γ-linoleic acid (GLA), using highly degenerate PCR against these histidine motifs. U.S. Pat. No. 5,614,393 (Rhone-Poulenc Agrochimie) discloses and claims the nucleotide sequence of borage $\Delta^6$ desaturase. Whilst the specification suggests that $\Delta^6$ desaturase-encoding nucleic acids might be isolated from animal cells without difficulty by the skilled person no suitable animal cells are suggested (in contrast to suggested fungal and bacterial cells) and there is no disclosure of the isolation of such nucleic acids from animal cells. The isolated DNA clone was shown by heterologous expression in transgenic tobacco to encode a microsomal $\Delta^6$ desaturase (Sayanova O et al (1997) *Proc. Natl. Acad. Sci.* USA. 94, 4211–4216). Desaturation at the $\Delta^6$ position is an unusual modification in higher plants, occurring only in a small number of species such as borage, evening primrose (*Oenothera* spp.) and redcurrant (*Ribes* spp.), which accumulate the $\Delta^6$-unsaturated fatty acids GLA and octadecatetraenoic acid (OTA:18:$^{4,6,6,9,12,15,}$ also known as stearidonic acid) in the seeds and/or leaves.

GLA is a high value plant fatty acid, and is widely used in the treatment of a number of medical conditions, including eczema and mastalgia It has been postulated that the application of GLA replaces the loss of, or meets an increased requirement for, endogenous $\Delta^6$-unsaturated fatty acids (Horrobin, D. F. (1990) *Rev. Contemp. Pharmacother.* 1: 1–45).

For reference purposes FIG. 5 is provided to show in simplified form a metabolic pathway believed to occur in certain organisms (including humans) and involving $\Delta^6$ desaturates. It can be seen that GLA can be synthesised in vivo from linoleic acid under the action of a $\Delta^6$ desaturase and that GLA can be used to synthesise dihomo-GLA, which can be converted to arachidonic acid under the influence of a $\Delta^5$ desaturase. Arachidonic acid is a precursor of various important eicosanoids (including prostaglandins and leucotrienes). $\Delta^6$ desaturase also converts a linoleic acid into OTA. Thus it is clear that the $\Delta^6$ desaturase is the first committed step on the biosynthetic pathway of these biologically active molecules (see FIG. 5).

The sequence of the previously isolated borage microsomal $\Delta^6$ desaturase differs from previously characterised plant microsomal desaturases/hydroxylases in that it contains an N-terminal extension which shows homology to cytochrome $b_5$, and also in that the third (most C-terminal) histidine box varies from the consensus (Shanklin J et al (1997) *Proc. Natl. Acad. Sci.* USA 94, 2981–1986) H-X-X-H-H, with a glutamine replacing the first histidine. This was also observed in the case of the cyanobacteria *Synechocystis* $\Delta^6$ desaturase (GenBank ID; L11421). WO93/06712 (Rhone Poulenc Agrochimie) discloses an isolated nucleic acid encoding a $\Delta^6$ desaturase isolated from the *Synechocystis*, and claims bacterial $\Delta^6$ desaturases and their uses.

Although $\Delta^6$ fatty acid desaturation is an unusual modification in higher plants, it is believed to be common in animals. The essential fatty acid linoleic acid (18:2 $\Delta^{9,12}$) is desaturated to GLA by a $\Delta^6$ desaturase as a first step in the biosynthetic pathway of the eicosanoids (which include prostaglandins and leucotrienes). This results in the rapid metabolism of GLA (to di-homo-GLA and arachidonic acid; i.e. 20:3$\Delta^{8,11,14}$ and 20:4 $\Delta^{5,8,11,14}$ respectively). Accumulation of GLA is therefore not usually observed.

The nematode worm *Caenorhabitis elegans* is extremely useful in that it has well understood genetics and has many similarities with higher animals such as humans and is therefore extremely useful in the development of desaturases for use in such animals.

According to the present invention, there is provided a polypeptide having desaturase activity, which comprises the amino acid sequence shown in FIG. 1 (SEQ ID NO:2).

The amino acid sequence shown in FIG. 1 (SEQ ID NO:2) is that of a $\Delta^6$ desaturase that is present in the nematode worm *Caenorhabitis elegans*. This is highly significant since prior to the present invention no successful sequencing or purification of an animal $\Delta^6$ desaturase had been reported. As *C. elegans* does not accumulate GLA isolation of a $\Delta^6$ desaturase from it was an unexpected target in which to isolate a desaturase gene.

The desaturase of the invention is significantly different from known desaturases. The homology between the $\Delta^6$ de of the invention and the microsomal $\Delta^{12}$ and $\Delta^{15}$ desaturases from *Arabidopsis* described in WO93/11245 are 24% and 16% respectively as determined using the BESTFIT program. The $\Delta^6$ desaturase gene of the present invention shows 21% identity with the *C.elegans* FAT-1 desaturase described in Spychalla, J. P. et al Proc. Natl Acad. Sci 94 1142–1147 M. The sequence homology between the $\Delta^6$ desaturase of the present invention and the *Synechochacystis* $\Delta^6$ described in WO93/06712 is only 23%.

According to another aspect of the invention there is provided therefore an isolated animal $\Delta^6$ desaturase.

The amino acid sequence shown in FIG. 1 (SEQ ID NO:2) is also of significance because it has a very low level of sequence identity with the borage $\Delta^6$ desaturase (the only other eukaryotic $\Delta^6$ desaturase to have been sequenced prior to the present invention). Indeed, this level of sequence identity is below 32%. At such a low level of identity it might be expected that the two polypeptides would have completely different functions. Unexpectedly, both have $\Delta^6$ desaturase activity.

The present invention is, however, not limited to a $\Delta^6$ desaturase having the sequence shown in FIG. 1 (SEQ ID NO:2). It includes other desaturases having at least 32% sequence identity therewith. Preferred polypeptides of the present invention have at least 40% or more, preferably at least 50% amino acid sequence identity therewith. More preferably the degree of sequence identity is at least 75%. Sequence identities of at least 90%, at least 95% or at least 99% are most preferred.

For the purposes of the present invention, sequence identity (whether amino acid or nucleotide) can be determined by using the "BESTFIT" program of the Wisconsin Sequence Analysis Package GCG 8.0.

Where high degrees of sequence identity are present there may be relatively few differences in amino acid sequence. Thus for example there may be less than 20, less than 10, or even less than 5 differences.

Fragments of the polypeptides described above are also within the scope of the present invention, provided that they have desaturase activity, that is to say they have the ability to introduce a double bond into a substrate at a specific position as determined by GCMS. What is the lowest limit for activity. These fragments are preferably at least 100 amino acids long More preferably, the fragments are at least 150 amino acids long.

In summary, a polypeptide of the present invention has desaturase activity and:]

a) comprises the amino acid sequence shown in FIG. 1 (SEQ ID NO:2);

b) has one or more amino acid deletions, insertions or substitutions relative to a polypeptide as defined in a) above, but has at least 32% amino acid sequence identity therewith; or c) is a fragment of a polypeptide as defined in a) or b) above, which is at least 100 amino acids long.

The term "polypeptide" is used herein in a broad sense to indicate that a particular molecule comprises a plurality of amino acids joined together by peptide bonds. It therefore includes within its scope substances, which may sometimes be referred to in the literature as peptides, polypeptides or proteins.

Desirably a polypeptide of the present invention will have a cytochrome domain. A cytochrome domain can be defined as an electron-transporting domain that contains a heme prosthetic group. Preferably a cytochrome b domain is present. More preferably a cytochrome $b_5$ domain is preset (desirably this includes a H-P-G-G-$X_{15}$-F-$X_{3-6}$-H (SEQ ID NO:3), where X is any amino acid, motif). A cytochrome $b_5$ domain is present in both the borage $\Delta^6$ desaturase and in the C. elegans $\Delta^6$ desaturase amino add sequence shown in FIG. 2B (SEQ ID NO:7). The cytochrome b5 domain is preferably an N-terminal domain—i.e. it is closer to the N-terminal end of the desaturase tan to the C-terminal end. This contrasts with other desaturases. For example, yeast $\Delta^9$ desaturase has a c-terminal cytochrome $b_5$ domain and plant $\Delta^{12}$ and $\Delta^{15}$ desaturases which do not have any $b_5$ domain.

A polypeptide of the present invention preferably has one or more (most preferably three) histidine boxes. One of these may have an H→Q substitution. (This provides a variant histidine box that is believed to be conserved over a range of animal/plant species.)

Polypeptides of the present invention can have any regiospecificity including cis/trans activity although it is preferred that they are front end desaturases that introduce a double bond between the C3 and C7 positions, measured from the COOH ($\Delta$ end) of the group. A skilled person is readily able to distinguish between different desaturases by determining the different positions of double bonds introduced by the desaturases. This can be done by known analytical techniques e.g. by using gas chromatography and mass spectrometry.

Particularly preferred desaturases of the invention are $\Delta^6$ desaturases.

Desirably the desaturases occur naturally in one or more organisms that do not accumulate GLA (i.e. where GLA may be produced, but is not normally detectable because it is very quickly metabolised). Such desaturases may occur naturally in one or more animals. The desaturases occur naturally in one or more nematodes, e.g. in C. elegans.

In order to appreciate the scope of the present invention more fully, polypeptides within the scope of each of a), b) and c) above will now be discussed in greater detail.

Polypeptides within the Scope of a)

A polypeptide within the scope of a) may consist of the amino acid sequence shown in FIG. 1 or may have an additional N-terminal and/or an additional C-terminal amino acid sequence.

Additional N-terminal or C-terminal sequences may be provided for various reasons and techniques for providing such additional sequences are well known in the art Such techniques include using gene-cloning techniques whereby nucleic acid molecules are ligated together and are then used to express a polypeptide in an appropriate host.

Additional sequences may be provided in order to alter the characteristics of a particular polypeptide. This can be useful in improving expression or regulation of expression in particular expression systems. For example, an additional sequence may provide some protection against proteolytic cleavage.

Additional sequences can also be useful in altering the properties of a polypeptide to aid in identification or purification. For example, a signal sequence may be present to direct the transport of the polypeptide to a particular location within a cell or to export the polypeptide from the cell. Different signal sequences can be used for different expression systems.

Another example of the provision of an additional sequence is where a polypeptide is linked to a moiety capable of being isolated by affinity chromatography. The moiety may be an epitope and the affinity column may comprise immobilised antibodies or immobilised antibody fragments that bind to said epitope (desirably with a high degree of specificity). The resultant fusion protein can usually be eluted from the column by addition of an appropriate buffer.

Additional N-terminal or C-terminal sequences may, however, be present simply as a result of a particular technique used to obtain a polypeptide of the present invention and need not provide any particular advantageous characteristic.

Polypeptides within the Scope of b)

Turning now to the polypeptides defined in b) above, it will be appreciated that these are variants of the polypeptides given in a) above.

Various changes can often be made to the amino acid sequence of a polypeptide which has a desired property in order to produce variants which still have that property. Such variants of the polypeptides described in a) above are within the scope of the present invention and are discussed in greater detail in sections (i) to (iii) below. They include allelic and non-allelic variants.

(i) Substitutions

An example of a variant of the present invention is a polypeptide as defined in a) above, apart from the substitution of one or more amino acids with one or more other amino acids.

The skilled person is aware that various amino acids have similar characteristics. One or more such amino acids of a polypeptide can often be substituted by one or more other such amino acids without eliminating a desired property of that polypeptide (such as desaturase activity).

For example, the amino acids glycine, alanine, valine, leucine and isoleucine can often be substituted for one another (amino acids having aliphatic side chains). Of these possible substitutions it is preferred that glycine and alanine are used to substitute for one another (since they have relatively short side chains) and that valine, leucine and isoleucine are used to substitute for one another (since they have lager aliphatic side chains which are hydrophobic). Other amino acids that can often be substituted for one another include phenylalanine, tyrosine and tryptophan (amino acids having aromatic side chains), lysine, arginine and histidine (amino acids having basic side chains); aspartate and glutamate (amino acids having acidic side chains); asparagine and glutamine (amino acids having amide side chains); and cysteine and methionine (amino acids having sulphur containing side chains).

Substitutions of this nature are often referred to as "conservative" or "semi-conservative" amino acid substitutions.

(ii) Deletions

Amino acid deletions can be advantageous since the overall length and the molecular weight of a polypeptide can be reduced whilst still retaining a desired activity. This can enable the amount of polypeptide required for a particular purpose to be reduced.

(iii) Insertions

Amino acid insertions relative to a polypeptide as defined in a) above can also be made. This may be done to alter the nature of the polypeptide (e.g. to assist in identification, purification or expression).

Polypeptides incorporating amino acid changes (whether substitutions, deletions or insertions) relative to the sequence of a polypeptide as defined in a) above can be provided using any suitable techniques. For example, a nucleic acid sequence incorporating a desired sequence change can be provided by site-directed mutagenesis. This can then be used to allow the expression of a polypeptide having a corresponding change in its amino acid sequence.

Polypeptides within the Scope of c)

As discussed supra, it is often advantageous to reduce the length of a polypeptide. Feature c) of the present invention therefore covers fragments of the polypeptides a) or b) above which are at least 100 amino acids long but which do not need to be as long as the full length polypeptide shown in FIG. 1 (SEQ ID NO:2). Desirably these fragments are at least 200, at least 300 or at least 400 amino acids long.

Various uses of the polypeptides of the present invention will now be described by way of example only.

Polypeptides of the present invention may be used, inter alia, in obtaining useful molecules. For example $\Delta^6$ desaturates can be used in obtaining γ-linolenic acid (GLA) or in obtaining metabolites in respect of which GLA is a precursor. For example, octadecatetraenoic acid (OTA; 18:4$\Delta^{6,9,12,15}$), a member of the n-3 (or ω-3) fatty acids may be produced by the $\Delta^6$-desaturation of α-linolenic acid.

GLA, OTA and their metabolites are useful in medicine. They can be used in the preparation of a medicament for treating a disorder involving a deficiency in GLA or of a metabolite derived in vivo from GLA (e.g. an eicosanoid). Disorders which may be treated include eczema, mastalgia, hypercholesterolemia, atherosclerosis, coronary disease, diabetic neuropathy, viral infections, acne, hypertension, cirrhosis and cancer.

The metabolites may be produced in vivo in suitable hosts or in vitro.

When a metabolite is to be produced in vitro, a desaturase of the present invention and its substrate will normally be provided separately and then combined when it is desired to produce the metabolite. The present invention therefore includes within its scope a method of making GLA or OTA comprising using a $\Delta^6$ desaturase of the present invention to convert linoleic acid substrate or α-linolenic acid substrate to GLA or OTA respectively.

When a metabolite is to be produced in vivo in a organism such as a plant or animal, the substrate for a desaturase of the present invention will normally be provided by the relevant non-human organism itself. In vivo production of the metabolite can therefor be achieved by inserting a gene encoding a desaturase of the present invention into the organism and allowing the organism to express the desaturase. The desaturase can then act on its substrate. It will therefore be appreciated that polypeptides of the present invention can be used to provide desaturase activity in organisms that would normally not possess such activity or to increase the level of desaturase activity in organisms already having some desaturase activity. If desired, a useful metabolite may be purified from such an organism. Alternatively the organism itself may be used directly as a souse of the metabolite. Particular cloning techniques that can be used to provide transgenic organisms with desaturase activity are discussed later on.

Polypeptides of the present invention can also be used as indicators of the transformation of an organism. For example, if an organism intended to be transformed does not have a particular desaturase and a nucleic acid intended for use in transformation encodes that desaturase, an assay can be performed after attempted transformation to determine whether or not the desaturase is present. Thus, in the case of the $\Delta^6$ desaturase, an assay for the presence of GLA may be performed and GLA can serve as a simple marker for the presence of a functional transgene cassette comprising a $\Delta^6$ desaturase encoding sequence.

A further use of the present invention is in providing antibodies. The present invention includes within its scope antibodies that bind to polypeptides of the present invention.

Preferred antibodies bind specifically to polypeptides of the present invention and can therefore be used to purify such polypeptides. (For example, they may be immobilised and used to bind to polypeptides of the present invention. The polypeptides may then be eluted by washing with a suitable eluent under appropriate conditions.)

An antibody or a derivative thereof within the scope of the present invention may be used in diagnosis. For example binding assays using such an antibody or a derivative can be used to determine whether or not a particular desaturase is present. This is useful in diagnosing disorders that arise due to the absence of the functional desaturase.

Antibodies within the scope of the present invention may be monoclonal or polyclonal.

Polyclonal antibodies can be raised by stimulating their production in a suitable animal host (e.g. a mouse, rat, guinea pig, rabbit, sheep, goat or monkey) when a polypeptide of the present invention is injected into the animal. If necessary an adjuvant may be administered together with a polypeptide of the present invention. The antibodies can then be purified by virtue of their binding to a polypeptide of the present invention.

Monoclonal antibodies can be produced from hybridomas. These can be formed by fusing myeloma cells and spleen cells which produce the desired antibody in order to form an immortal cell line. Thus the well-known Kohler & Milstein technique (*Nature* 256 52–55 (1975)) or variations upon this technique can be used.

Techniques for producing monoclonal and polyclonal antibodies that bind to a particular polypeptide are now well developed in the art. They are discussed in standard immunology textbooks, for example in Roitt et at, *Immunology* second edition (1989), Churchill Livingstone, London.

In addition to whole antibodies, the present invention includes derivatives thereof which are capable of binding to polypeptides of the present invention. Thus the present invention includes antibody fragments and synthetic constructs. Examples of antibody fragments and synthetic constructs arm given by Dougall et al, in *Tibtech* 12 372–379 (September 1994).

Antibody fragments include, for example, Fab, F(ab')$_2$ and Fv fragments. (cbese are discussed, for example, in Roitt et al (supra)). Fv fragments can be modified to produce a synthetic construct known as a single chain Fv (scFv) molecule. This includes a peptide linker covalently joining $V_h$ and $V_1$ regions, which contributes to the stability of the molecule. Other synthetic constructs that can be used include CDR peptides. These are synthetic peptides comprising antigen-binding determinants. Peptide mimetics may also be used. These molecules are usually conformationally restricted organic rings that mimic the structure of a CDR loop and that include antigen-interactive side chains.

Synthetic constructs include chimaeric molecules. Thus, for example, humanised (or primatised) antibodies or derivatives thereof are within the scope of the present invention. An example of a humanised antibody is an antibody having human framework regions, but rodent hypervariable regions.

Synthetic constructs also include molecules comprising an additional moiety which provides the molecule with some desirable property in addition to antigen binding. For example the moiety may be a label (e.g. a fluorescent or radioactive label). Alternatively, it may be a pharmaceutically active agent.

The present invention also includes nucleic acid molecules within its scope.

Such nucleic acid molecules:

a) code for a polypeptide according to the present invention; or b) are complementary to molecules as defined in a) above; or c) hybridise to molecules as defined in a) or b) above.

These nucleic acid molecules and their uses are discussed in greater detail below:

The polypeptides of the present invention can be coded for by a large variety of nucleic acid molecules, taking into account the well-known degeneracy of the genetic code. All of these coding nucleic acid molecules are within the scope of the present invention. Preferred coding nucleic acid molecules encode the polypeptide shown in FIG. 1. These include nucleic acid molecules comprising the coding sequence shown in FIG. 1 and degenerate variants thereof.

The nucleic acid molecules may be used directly. Alternatively they may be inserted into vectors.

Nucleic acids or vectors containing them may be used in cloning. They may be introduced into non-human hosts to enable the expression of polypeptides of the present invention using techniques known to those skilled in the art. Alternatively, cell free expression systems may be used.

Techniques for cloning, expressing and purifying polypeptides are well known to the skilled person. Various such techniques are disclosed in standard text-books, such as in Sambrook et al (*Molecular Cloning* 2nd Edition, Cold Spring Harbor Laboratory Press (1989)); in Old & Primrose (*Principles of Gene Manipulation,* 5th Edition, Blackwell Scientific Publications (1994)); and in Stryer (*Biochemistry,* 4th Edition, W H Freeman and Company (1995)).

By using an appropriate expression system the polypeptides can be produced in a desired form. For example, the polypeptides can be produced by microorganisms such as bacteria or yeast, by cultured insect cells (which may be baculovirus-infected), or by mammalian cells (such as CHO cells).

However preferred hosts are plants or plant propagating material e.g. oil seed rape, sunflower, cereals including maize, tobacco, legumes including peanut and soybean, safflower, oil palm, coconut and other palms, cotton, sesame, mustard, linseed, castor, borage and evening primrose, or propagating material therefor.

The technology for providing plants or plant propagating material is now well developed. It is briefly discussed in WO 96/21022, for example. Desaturases isolated from animals have success fully been expressed in plants. For example, Spychalla, J. P. et al, (supra) describe the expression of a *C. elegans* desaturase in transgenic *Arabidopsis*. Additionally, EP0550162 (Pioneer Hi-Bred International, Inc) discloses a chimaeric gene construct encoding a $\Delta^9$ desaturase isolated from rat, and plants transformed with the construct for the production of fatty acids. The desaturase described in that publication has only 22% identity with the $\Delta^6$ desaturase of the present invention.

Particular techniques that can be used are discussed below. It will of course be appreciated that such techniques are non-limiting.

(i) Vector Systems Based on *Agrobacterium Tumefaciens*.

These include Ti based systems, such as pGV3850, in which the T-DNA has been disarmed. Desirably a selectable marker is present (e.g. a marker that provides resistance to an antibiotic).

Intermediate vectors (IVs) may also be used They tend to be small in size and are therefore usually easier to manipulate than large Ti based vectors. IVs are generally vectors resulting from T-DNA having been cloned into *E. coli* derived plasmid vectors, such as pBR322. IVs are often conjugation-deficient and therefore a conjugation-proficient plasmid (such as pRK2013) may be used to mobilise an IV so that it can be transferred to an *Agrobacterium* recipient. In vivo homologous recombination can then occur in an *Agrobacterium* to allow an IV to be inserted into a resident, disarmed Ti plasmid in order that a cointegrate can be produced that is capable of replicating autonomously in the *Agrobacterium*.

Another alternative is to use binary Ti vectors. Here a modified T-DNA region carrying foreign DNA can be provided on a small plasmid that replicates in *E. coli* (e.g. pRK252). This plasmid (sometimes called mini-Ti or micro-Ti) can then be transferred conjugatively via a tri-parental mating into an *A. tumefaciens* that contains a compatible vir gene (providing the vir function in trans).

Binary vectors without Ti sequences may even be used. Here bacterial mob and oriT functions may be used to promote plasmid transfer. Again, the vir function may be provided in trans.

The vector systems discussed above can be used to transfer genes into plants by using the protocol of Horsch et al. (*Science* 227, 1229–31 (1985)) or variants thereof. Here small discs can be punched from the leaves of a dicotyledenous plant, they can be surface-sterilised, and can then be placed in a medium including *A. tumefaciens* that contains recombinant T-DNA in which a foreign gene to be transferred is accompanied by a selectable marker (e.g. the neo gene). The discs can then be cultured for 2 days and then transferred to a medium for selecting the selectable marker. (This can be done for a neo selectable marker by culturing using a medium containing kanamycin). *A. tumefaciens* can be killed by using a carbenicillin containing medium. Shoots will normally develop from a callus after 2–4 weeks. They can then be excised and transplanted to root-inducing medium and, when large enough can be transplanted into soil.

(ii) Vector Systems Based on *Agrobacterium Rhizogenes*

These include Ri derived plasmids. Ri T-DNA is generally considered not to be deleterious and therefore such plasmids can be considered as equivalent to disarmed Ti plasmids. An IV cointegrate system based on Ri plasmids has been developed.

(iii) Plant Protoplast Based Transformation Systems

Suitable techniques are described in "Plant Gene Transfer and Expression Protocols" ed. H Jones, Human Press Methods in Molecular Biology, 49, 1995.

Transformation of plants can be facilitated by moving plant cell walls to provide protoplasts. The cell walls can be removed by any suitable means, including mechanical disruption or treatment with cellulolytic or pectinolytic enzymes. Protoplasts can then be separated from other components by centrifugation and techniques such as electroporation can then be used to transform the protoplasts with heterologous DNA. Under appropriate culture conditions the transformed protoplasts will grow new cell walls and also divide. Shoots and roots can then be induced and plantlets formed.

(iv) Transfection by Biolistics

High velocity microprojectiles carrying DNA or RNA can be used to deliver that DNA or RNA into plant cells. This has allowed a wide variety of transgenic plants to be produced and is suitable for both monocotyledenous and dicotyledenous plants. For example gold or tungsten particles coated with DNA or RNA can be used. Suitable devices for propelling the microprojectiles include gunpowder based devices, electric discharge based devices and pneumatic devices.

(v) Virus Based System

DNA plant virus vectors include cauliflower mosaic viruses (which infect a range of dicots.) and geminiviruses (which infect a wide range of dicots. and monocots). RNA plant viruses are in the majority and include Brone Mosaic Virus (which infects a number of Graminae, including barley) and Tobacco Mosaic Virus (which infects tobacco plants).

From the foregoing description it will be appreciated that nucleic acid molecules encoding polypeptides of the present invention can be cloned and expressed in a wide variety of organisms.

In addition to nucleic acid molecules coding for polypeptides of the present invention (referred to herein as "coding" nucleic acid molecules), the present invention also includes nucleic acid molecules complementary thereto. Thus, for example, both strands of a double stranded nucleic acid molecule are included within the scope of the present invention (whether or not they are associated with one another). Also included are mRNA molecules and complementary DNA molecules (e.g. cDNA molecules).

Nucleic acid molecules that can hybridise to one or more of the nucleic acid molecules discussed above are also covered by the pot invention. Such nucleic acid molecules are referred to herein as "hybridising" nucleic acid molecules.

A hybridising nucleic acid molecule of the present invention may have a high degree of sequence identity along its length with a nucleic acid molecule within the scope of a) or b) above (e.g. at least 50%, at least 75% or at least 90% sequence identity).

As will be appreciated by those skilled in the art, the greater the degree of sequence identity that a given single stranded nucleic acid molecule has with another single stranded nucleic acid molecule, the greater the likelihood that it will hybridise to a single stranded nucleic acid molecule which is complementary to that other single stranded nucleic acid molecule under appropriate conditions.

Desirably hybridising molecules of the present invention are at least 10 nucleotides in length and preferably are at least 25, at least 50, at least 100 or at least 200 nucleotides in length.

Preferred hybridising molecules hybridise under stringent hybridization conditions. One example of stringent hybridisation conditions is where attempted hybridisation is carried out at a temperature of from about 35° C. to about 65° C. using a salt solution that is about 0.9 molar. However, the skilled person will be able to vary such parameters as appropriate in order to take into account variables such as probe length, base composition, type of ions present, etc.

Most preferably, hybridising nucleic acid molecules of the present invention hybridise to a DNA molecule having the coding sequence shown in FIG. 1 to an RNA equivalent thereof or to a complementary sequence to either of the aforesaid molecules.

Hybridising nucleic acid molecules can be useful as probes or primers, for example.

Probes can be used to purify and/or to identify nucleic acids. For example they can be used to identify the presence of all or part of a desaturase gene and are therefore useful in diagnosis.

Primers are useful in amplifying nucleic acids or parts thereof, e.g. by PCR techniques.

In addition to being used as probes or primers, hybridising nucleic acid molecules of the present invention can be used as antisense molecules to alter the expression of polypeptides of the present invention by binding to complementary nucleic acid molecules. (Generally this can be achieved by providing nucleic acid molecules that bind to RNA molecules that would normally be translated. thereby preventing translation due to the formation of duplexes.)

Hybridising molecules may also be provided as ribozymes. Ribozymes can also be used to regulate expression by binding to and cleaving RNA molecules that include particular target sequences recognised by the ribozymes.

From the foregoing discussion it will be appreciated that a large number of nucleic acids are within the scope of the present invention. Unless the context indicates otherwise, nucleic acid molecules of the present invention may therefore have one or more of the following characteristics:

1) They may be DNA or RNA (including variants of naturally occurring DNA or RNA structures, which have non-naturally occurring bases and/or non-naturally occurring backbones).
2) They may be single or double stranded.
3) They may be provided in recombinant form i.e. covalently linked to a heterologous 5' and/or 3' flanking sequence to provide a chimaeric molecule (e.g. a vector) which does not occur in nature.
4) They may be provided without 5' and/or 3' flanking sequences that normally occur in nature.

5) They may be provided in substantially pure form, e.g. by using probes to isolate cloned molecules having a desired target sequence or by using chemical synthesis techniques. Thus they may be provided in a form which is substantially free from contaminating proteins and/or from other nucleic acids.

6) They may be provided with introns (e.g. as a full-length gene) or without introns (e.g as cDNA).

The present invention will now be described by way of example only, with reference to the accompanying drawings, FIGS. 1 to 6 wherein:

FIG. 1 shows the DNA sequence and the deduced amino acid sequence of the full length C. elegans cDNA pCeD6.1. The positions of the N-terminal cytochrome $b_5$ domain and the variant third histidine box are underlined. The deduced amino acid sequence of this cDNA is identical to that predicted for residues 1–38 and 68–473 of W08D2.4.

FIG. 2A shows a comparison of the deduced amino acid sequences of the C. elegans cDNA CeD6.1 and the C. elegans predicted protein W08D2.4. (MywormD6=CeD6.1; cew08d2=ORF W08D2.4.)

FIG. 2B shows a comparison of the deduced amino acid sequences of the borage $\Delta^6$ desaturase (Sayanova O et al (1997) Proc. Natl. Acad. Sci. USA 94, 4211–4216) and the C. elegans cDNA CeD6.1. (Boofd6=Borage officianalis $\Delta^6$ desaturase, ceeld6=CeD6.1.)

FIG. 4 shows GC-MS analysis of the novel peak identified in yeast carrying pYCeD6.1.

EXAMPLE 1

Figure 3A:
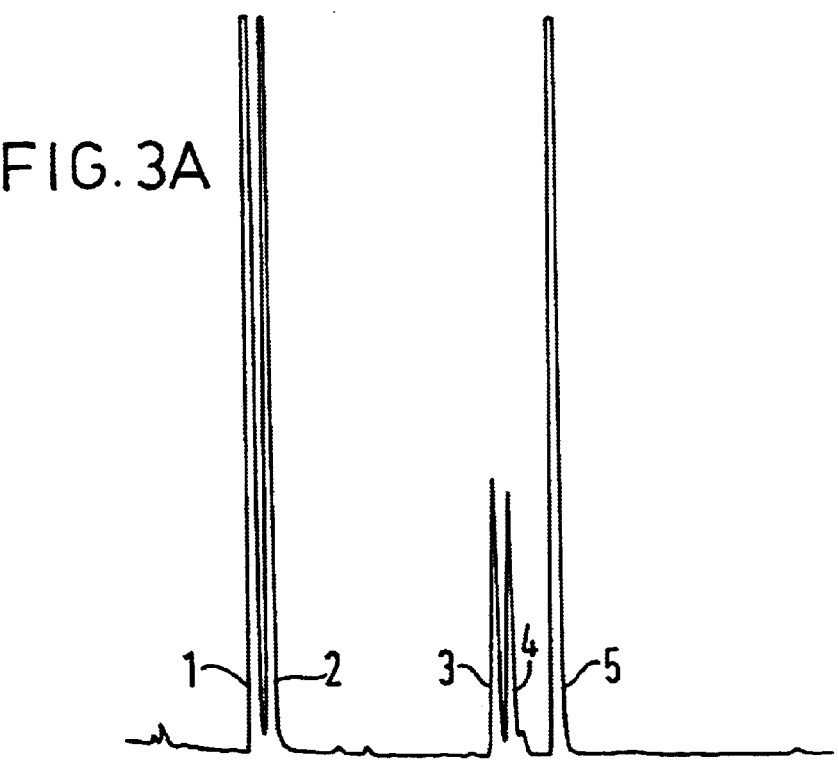
FIG. 3 shows methyl esters of total lipids of S. cerevisiae grown under inducing conditions (linololate and galactose).

Isolation of $\Delta^6$ Desaturase Gene and Expression in Yeast

The NCBI EST sequence database was searched for amino acid sequences using a known borage $\Delta^6$ fatty acid desaturase (Sayanova O et al (1997) supra) and limiting the search to sequences containing a variant histidine box Q-X-X-H-H. C. elegans ESTs were identified. They were further characterised by searching the C. elegans EST project database (Prof. Y. Kohara lab (National Institute of Genetics, Mishima, Japan); DNA Database of Japan) to identify related cosmid clones.

A partial 448 base pair cDNA clone designated as yk436b12 identified by these searches was obtained from the C. elegans EST project, and this was used to screen a C. elegans cDNA library (mixed stage; also supplied by Prof Kohara) This indicated that the clone yk436bb12 was homologous to part of a gene present on cosmid W08D2 (Genbank accession number Z70271), which forms part of chromosome IV. Bases 21-2957 of cosmid W0D2 are predicted by the protein prediction program Genefinder (Wilson R et al (1994) Nature 368 32–38 to encode an ORF of 473 residues which is interrupted by 5 introns. Wilson, R. et al disclose part of the sequence of chromosome m of C. elegans. A number of positives were identified and further purified, and full length clones were confirmed by sequencing to encode a transcript likely to have been transcribed from the gene designated W08D2.4, on cosmid W08D2, as determined by database searching of the genes sequenced by the C. elegans genome project Examination of this predicted polypeptide (designated W08D2.4 by the Sanger Centre Nematode Sequencing Project, Hinxton, UK) revealed that it had a number of characteristics reminiscent of a microsomal fatty acid desaturase, including three histidine boxes. However, the predicted protein sequence indicated the presence of an N-terminal domain similar to cytochrome bs, containing the diagnostic H-P-G-G motif found in cytochrome $b_5$ proteins (Lederer F (1994) Biachimie. 76, 674–692). Since the $\Delta^6$ desaturase isolated by us from borage also contained an N-terminal $b_5$ domain, this indicated that W0D2.4 may encode a $D^6$ desaturase.

Closer examination of the sequence revealed the presence of the variant third histidine box, with an H→Q substitution (again as observed in the borage $\Delta^6$ desaturase). The degree of similarity between W08D2.4 and the borage $\Delta^6$ desaturase is <52% and is therefore low. The figure of <31% obtained for identity is also low.

Since W08D2.4 was encoded by a gene containing many (6) introns, it was necessary to isolate a full length cDNA to verify the sequence predicted by the Genefinder program and to also allow the expression of the ORF to define the encoded function.

A cDNA library was screened with the EST insert yk436b12 (generously provided by Prof Y. Kohara) and a number of positive plaques were identified. These were further purified to homogeneity, excised, and the largest inserts (of ~1450 bp) from the resulting rescued phagemids were sequenced. This confirmed that the cDNAs isolated by us were indeed homologous to W08D2.4, with the 5' and 3' ends of the cDNA being equivalent to bases 9 and 3079 of the sequence of cosmid W08D2. Since the ATG initiating codon predicted by the Genefinder program to be the start of gene product W08D2.4 was indeed the first methionine in the cDNA clone, we reasoned that we had isolated a bonafide full length cDNA. The DNA sequence and deduced amino acid sequence of one representative cDNA clone (termed pCeD6.1; 1463 bp in length) is shown in FIG. 1; the deduced amino acid sequence is identical to that predicted for W08D2.4 over the majority of the protein. The positions of the N-terminal cytochrome $b_5$ domain and the variant third histidine box are underlined The deduced amino acid sequence of this cDNA is identical to that predicted for residues 1–38 and 68–473 of W08D2.4.

Figure 2A:
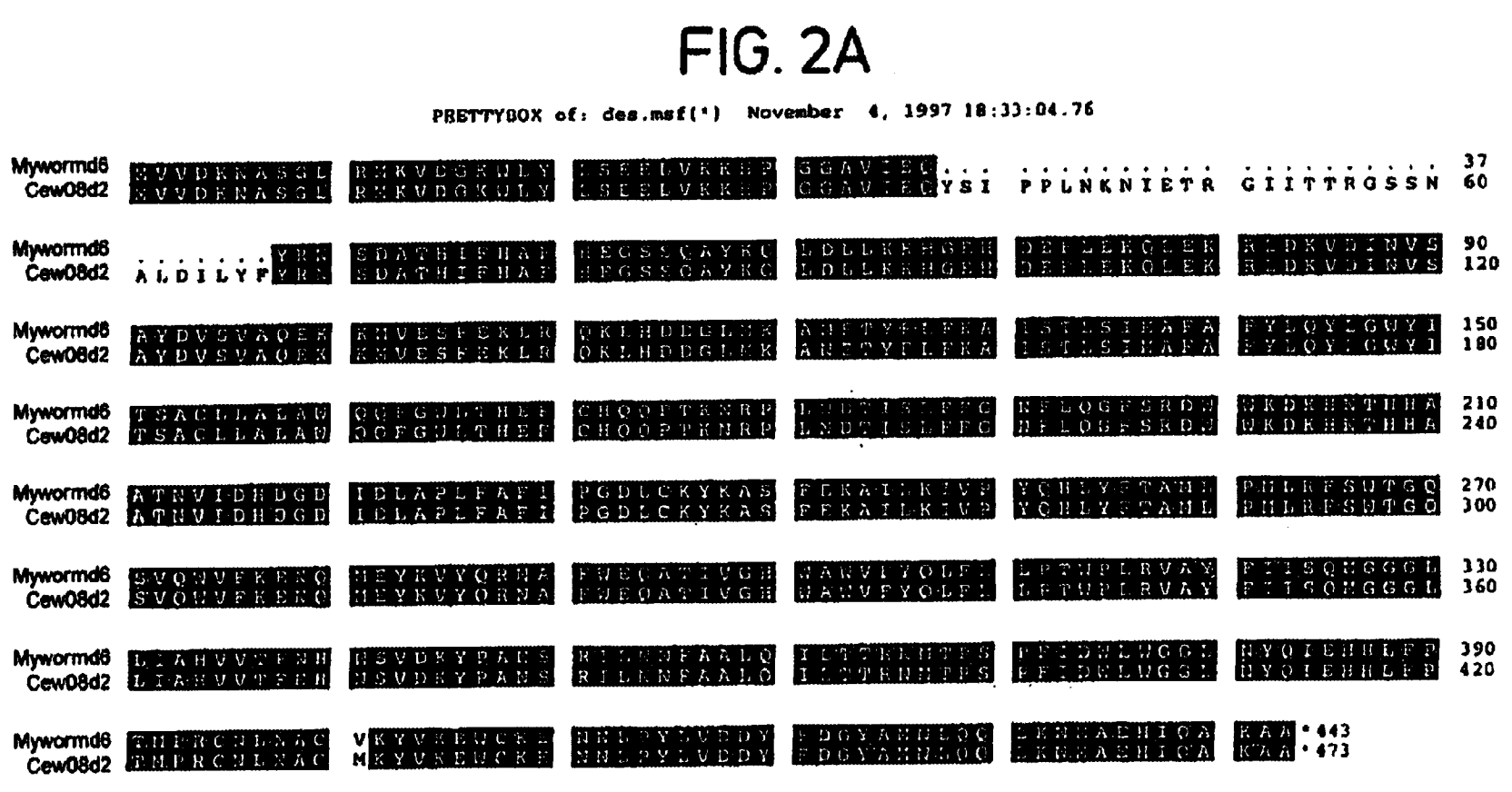
Figure 2B:
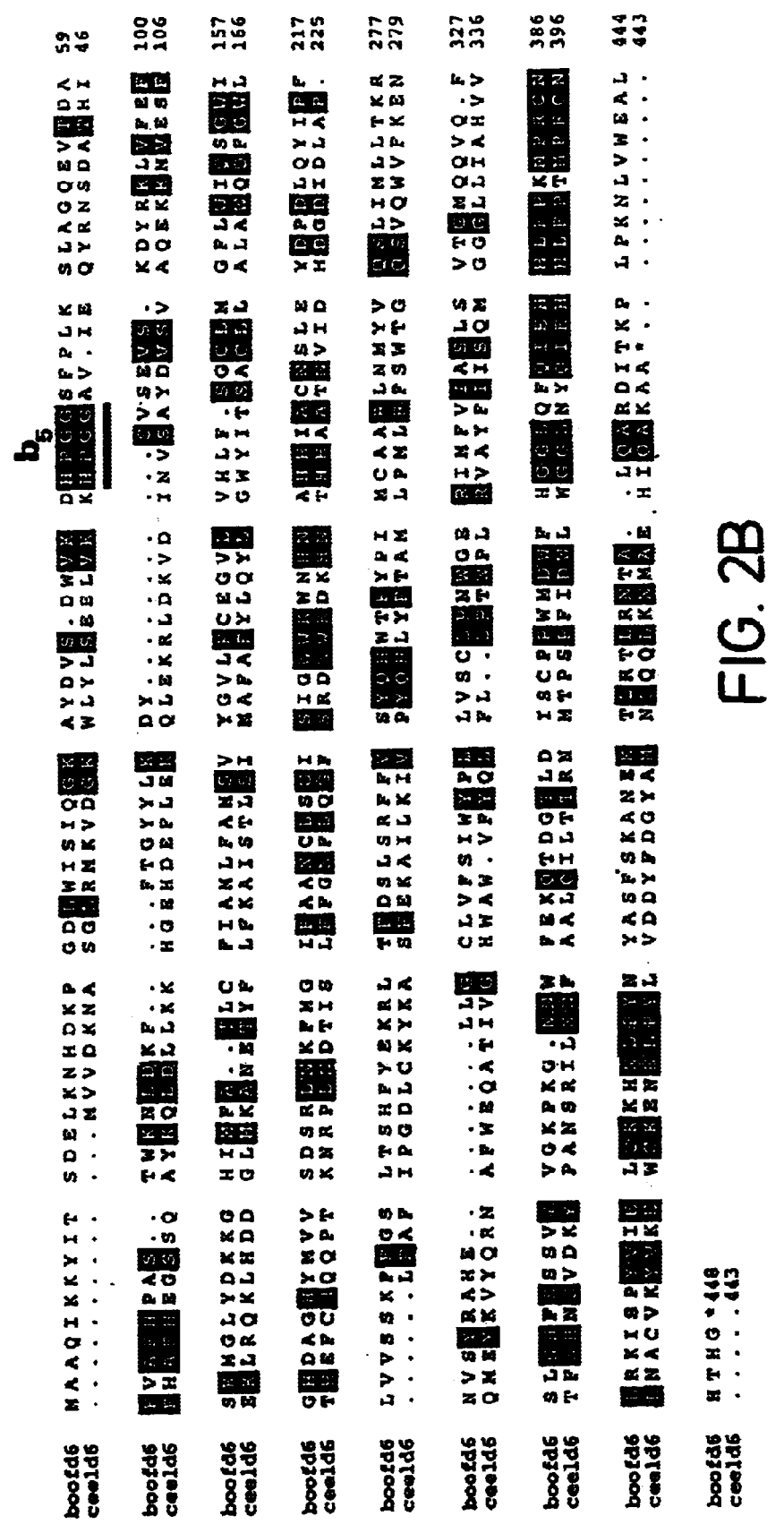

However, DNA sequences encoding residues 38–67 Y-S-I . . . L-Y-F) predicted for W08D2.4 are not present in the cDNA clone This means that the deduced amino acid sequence of CeD6.1 is in fact 443 amino acids long (SEQ ID NO:4), as opposed to that predicted for W08D2.4, which is 473 residues in length (SEQ ID NO:5). The only other difference between the two amino acid sequences is an M→V sub I on at residue 401, resulting from an A→G base change (base 1211). The two sequences are compared in FIG. 2A (SEQ ID NOS:4 and 5), as is the deduced amino acid sequence of the borage $\Delta^6$ desaturase (SEQ ID NO:6) and that of C3D6.1 (SEQ ID NO:7) (FIG. 2B). The extra sequence predicted for W08D2.4 is likely derived from incorrect prediction of intron-exon borders.

The coding sequence of W08D2.4 was introduced into the yeast expression vector pYES2 by PCR. Oligonucleotides with 5' overhangs were used to introduce KpnI and SacI sites at the 5' and 3' ends respectively. The fidelity of the construct was checked by in vitro transcription and translation using the TnT system (Promega).

Specifically, clone pCeD6.1 was then used as a template for PCR amplification of the entire predicted coding sequence (443 amino acid residues in length), and cloned into the yeast expression vector pYES2 (Invitrogen) to yield pYCeD6. The fidelity of this PCR-generated sequence was checked in vitro transcription/translation of the plasmid, using the T7 RNA polymerase promoter present in pYES2.

Using the Promega TnT coupled transcription/translation system, translation products were generated and analysed by SDS-PAGE and autoradiography as per the manufacturer's instructions. This revealed (data not shown) that the plasmid pYCeD6 generated a product of ~55 kD, whereas the control (pYES2) failed to yield any protein products, indicating that the construct was correct.

The resulting plasmid was introduced into yeast (*S. cerevisiae*) by the lithium acetate method (Guthrie C, Fink G R (1991) *Meths Enz* 194) and expression of the transgene was induced by the addition of galactose. The yeast was supplemented by addition of 0.2 mM linoleate (sodium salt) in the presence of 1% tergitol NP40.

Transformation and selection of yeast able to grow on uracil-deficient medium revealed yeast colonies carrying the recombinant plasmid pYCeD6 by virtue of the URA3 selectable marker carried by pYES2. Expression of pYCeD6 was obtained by inducing the GAL promoter that is present in pYES2. This was carried out after the cells had been grown up overnight with raffinose as a carbon source, and the medium supplemented by the addition of linoleate (18:2) in the presence of low levels of detergent. This later addition was required since the normal substrate for $\Delta^6$ desaturation is 18:2 fatty acids, which do not normally occur in *S. cerevisiae*.

Yeast total fatty acids were analyzed by GC of methyl esters. Confirmation of the presence of GLA was carried out by GC-MS (Sayanova et al (1997) supra).

Figure 3B:
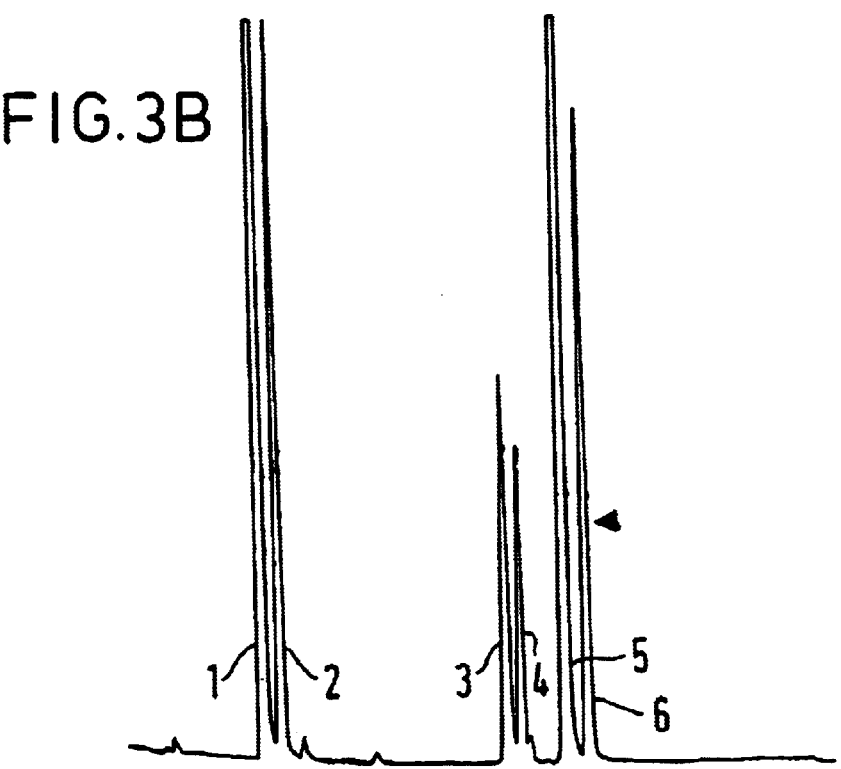
Figure 5:
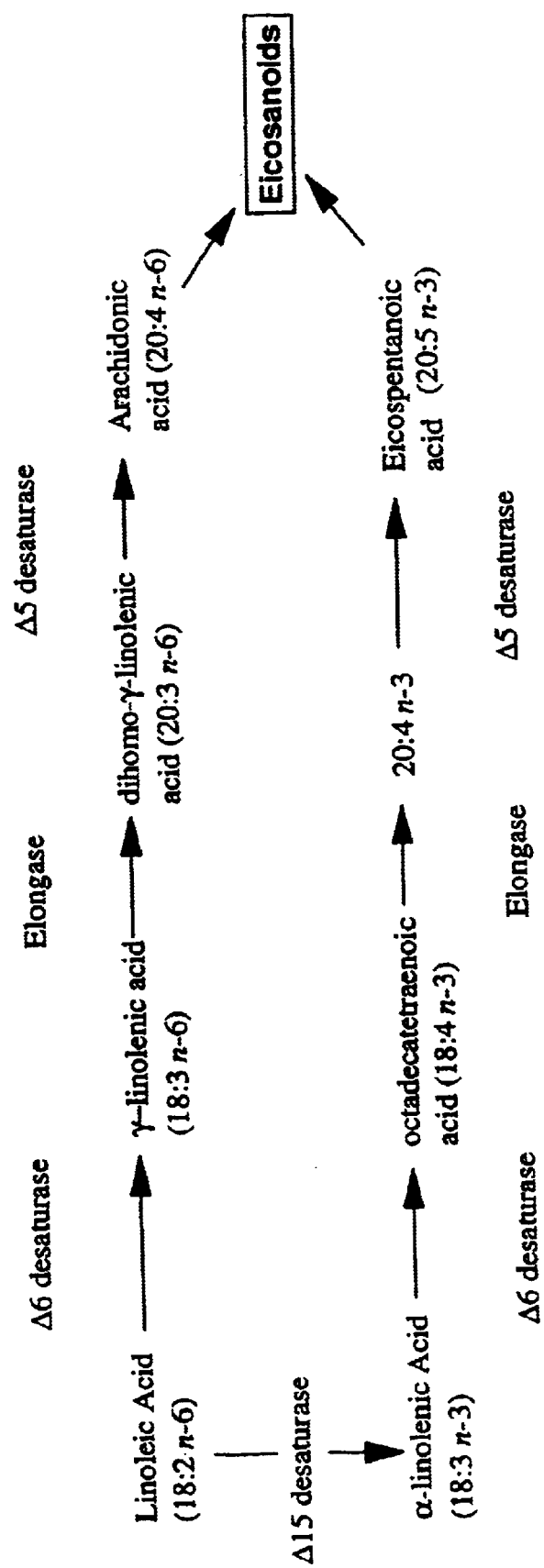
FIG. 5 shows a simplified version of the metabolism of n-6 essential fatty acids in mammals.

In more detail, the cultures were then allowed to continue to grow after induction, with aliquots being removed for analysis by GC. When methyl esters of total fatty acids isolated from yeast carrying the plasmid pYCeD6 and grown in the presence of galactose and linoleate were analyzed by GC, an additional peak was observed (FIG. 3). In FIG. 3 Panel A is yeast transformed with control (empty) vector pYES2, panel B is transformed with pYCeD6.1. The common fatty acid-methyl esters were identified as 16:0 (peak 1), 16:1 (peak 2), 18:0 (peak 3), 18:1 (peak 4), 18:2 (peak 5; supplied exogenously). The additional peak (6) in panel B corresponds to 18:3 GLA, and is indicated by an, arrowhead. This had the same retention time as an authentic GLA standard, indicating that the transgenic yeast were capable of $\Delta^6$-desaturating linoleic acid. No such peaks were observed in any of the control samples (transformation with pYES2). The identity of this extra peak was confirmed by GC-MS, which positively identified the compound as GLA (FIG. 4). In the FIG. 4 experiment, the sample was analyzed for mass spectra as before (Sayanova O et al (1997) *Proc. Natl. Acad. Sci. USA* 94, 4211–4216), and the data used to search a library of profiles. The sample was identified as GLA. A comparison of the mass spectra of the novel peak (A) and authentic GLA (B) is shown; visual and computer-based inspection revealed them to be identical. This confirms that CeD6.1 encodes a *C. elegans* $\Delta^6$ desaturase, and that this cDNA is likely to be transcribed from the gene predicted to encode ORF W08D2.4, though the deduced amino acid sequence of CeD6.1 is 30 residues smaller than that of W08D2.4

EXAMPLE 2

Expression of *C.elegans* $\Delta^6$ Desaturase in Plants

Figure 6A:
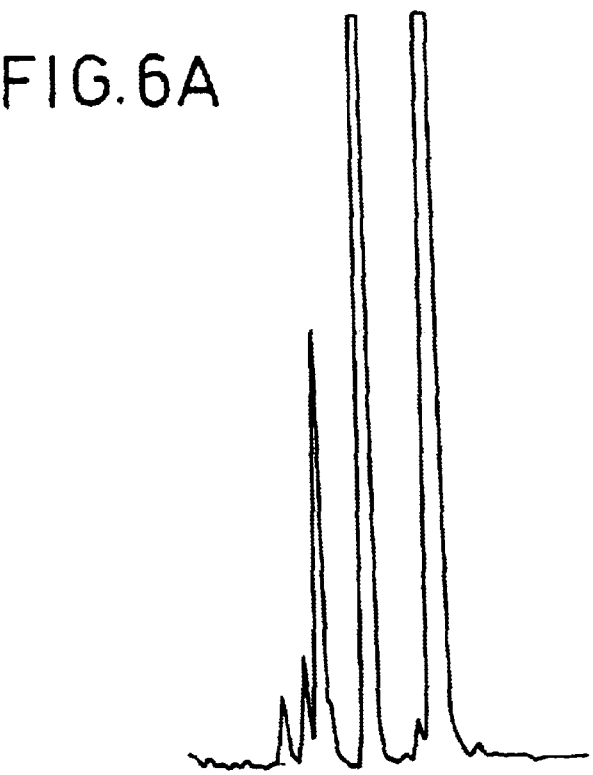
FIG. 6 shows fatty acid and methyl esthers of leaf material from either control transformed Arabidopsis plant (A) or transformed Arabidopsis plant expressing the C. elegans$\Delta^6$ desaturase (B).
Figure 6B:
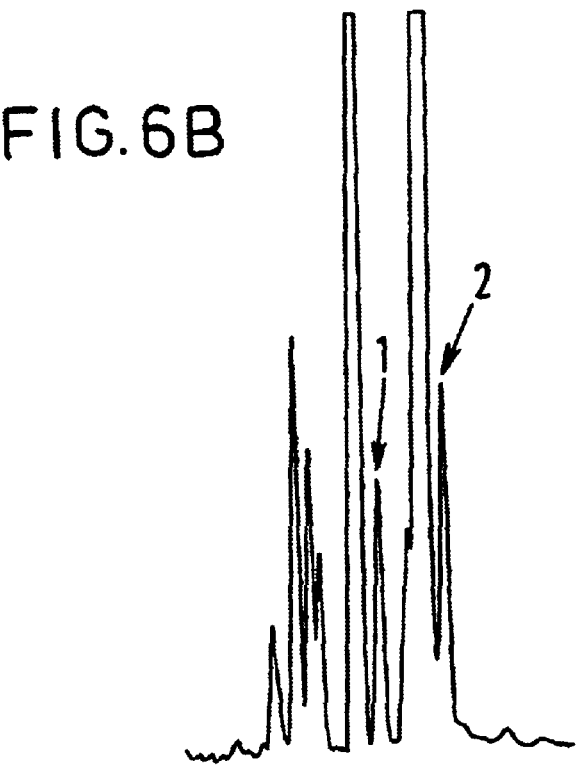

The coding sequence of the *C. elegans* $\Delta^6$ desaturates was subcloned into a plant expression vector pJD330, which comprises a viral 35S promoter, and a Nos terminator. The resulting cassette or promoter/coding sequence terminator was then subcloned into the plant binary transformation vector pBin 19, and the resulting plasmid was introduced into *Agrobacterium tumefaciens*. This *Agrobacterium* strain was then used to transform *Arabidopsis* by the vacuum-infiltration of inflorescences. Seeds were harvested and plated onto selective media containing kanamycin. Since pBin 19 confers resistance to this antibiotic, only transformed plant material will grow. Resistant lines were identified and self-fertilized to produce homozygous material. Leaf material was analyzed for fatty acid profiles using the same method as used for the expression of the nematode desaturase in yeast Fatty acid methyl esthers were separated by GC, and novel peaks shown in FIG. 6 identified by comparison with known standards and GCMS. Two novel peaks can be seen in (B) which were identified as $\gamma$-linolenic acid (peak 1) and octadecatetraenoic acid (peak 2). These are the products of $\Delta^6$ desaturation of the precursor fatty acids linoleic acid and $\alpha$-linolenic acid, respectively.

The inventors have shown that a *C. elegans* cDNA (CeD6.1) encodes a $\Delta^6$ desaturase, and that this sequence is identical with the predicted ORF W08D2.4, except for a 30 residue insertion present in the N-terminal region of the latter protein. Whether the deduced amino acid sequence predicted for CeD6.1 represents a splicing variant of W08D2.4, or is a result of a mis-prediction of the intron/exon junctions by the Genefinder programme is unclear. However it is clear that CeD6.1 encodes a $\Delta^6$ desaturase.

The ORF encoded by the this *C. elegans* sequence appears to be related to the higher plant $\Delta^6$ fatty acid desaturase previously isolated by us (Sayanova O et al (1997) supra), in that they both contain N-terminal domains which show homology to cytochrome $b_5$. Microsomal fatty acid desaturases have been demonstrated to use free microsomal cytochrome bg as their electron donor (Smith M A, et al (1990) *Biochem. J.* 272, 23–29, Smith M A et al (1992) *Biochem. J.* 287, 141–144)), and the vast majority of identified sequences for these enzymes appear not to contain this additional cytochrome $b_5$ domain (Okuley J et al (1994) *Plant Cell* 6, 147–158, Aronel V. et al (1992) *Science* 258, 1353–1355 and Napier, J. A. et al (1997) *Biochemical J*, 328:717–8).

Prior to the present invention only two examples of cytochrome $b_5$-domain-containing desaturases were known, one being the borage $\Delta^6$ desaturase, and the other being the yeast microsomal $\Delta^9$ (OLE1) desaturase (Napier J A et al (1997) *Biochemical J*, supra and Mitchell A G, Martin C E (1995) *J. Biol. Chem* 270, 29766–29772). OLE1, however, contains a C-terminal cytochrome $b_5$ domain (Napier J A et al (1997) *Biochemical J*, in press and Mitchell A G, Martin C E (1995) *J. Biol. Chem.* 270, 29766–29772). The reason for the cytochrome be may be that the $\Delta^6$ desaturase is a "front-end" desaturase. (A "front-end" desaturation can defined as the final desaturation reaction on the fatty acid chain, usually introducing double bonds between a preexisting bond and the $\Delta$-end of the carboxy group (Mitchell A G, Martin C E (1995) *J. Biol. Chem* 270, 29766–29772 and Aitzetmuller K, Tseegsuren, N (1994) *J. Plant Physiol.* 143, 538–543).)

In any event, it is now believed to be the case that both a variant histidine box and an N-terminal cytochrome $b_5$ domain are conserved in both animals and plants, as evidenced by their presence in both the borage and nematode $\Delta^6$ desaturases.

The invention may therefore allow the identification of other $\Delta^6$ desaturases and also other "front-end" desaturases to be identified by the presence of these motifs.

What is claimed is,:

1. An isolated and purified polypeptide having $\Delta^6$ desaturase activity which comprises an amino acid sequence that is at least 95% identical to SEQ ID NO: 2.

2. A polypeptide according to claim 1, which has a cytochrome $b_5$ domain.

3. A polypeptide according to claim 1, which comprises a histidine box.

4. A polypeptide according to claim 1, which occurs naturally in *C. elegans*.

5. A polypeptide according to claim 1, which is covalently linked to a moiety capable of being isolated by affinity chromatography.

6. An isolated and purified $\Delta^6$ desaturase polypeptide comprising the amino acid sequence as shown in SEQ ID NO:2 with no more than five conservative amino acid substitutions.

7. The polypeptide of claim 6 which has one conservative amino acid substitution.

8. The polypeptide of claim 6 which comprises the amino acid sequence as shown in SEQ ID NO:2.

9. The polypeptide of claim 1 which is covalently linked to a moiety capable of being isolated by affinity chromatography.

10. The polypeptide of claim 8 further comprising a signal sequence.

11. The polypeptide of claim 1 which has at least 99% amino acid sequence identity with the amino acid sequence of SEQ ID NO:2.

12. An isolated and purified polypeptide having $\Delta^6$ desaturase activity, which comprises a fragment of SEQ ID NO: 2, wherein said fragment has $\Delta^6$ desaturase activity.

* * * * *

UNITED STATES PATENT AND TRADEMARK OFFICE
CERTIFICATE OF CORRECTION

PATENT NO. : 6,897,050 B1
DATED : May 24, 2005
INVENTOR(S) : Johnathan A. Napier It is certified that error appears in the above-identified patent and that said Letters Patent is hereby corrected as shown below:

Column 32,
Line 5, replace "claim 1" with -- claim 6 --.

Signed and Sealed this

Thirteenth Day of June, 2006

JON W. DUDAS
*Director of the United States Patent and Trademark Office*